(12) United States Patent
Honda et al.

(10) Patent No.: US 9,568,439 B2
(45) Date of Patent: Feb. 14, 2017

(54) DEFECT INSPECTION DEVICE AND DEFECT INSPECTION METHOD

(71) Applicant: Hitachi High-Technologies Corporation, Tokyo (JP)

(72) Inventors: Toshifumi Honda, Tokyo (JP); Yuta Urano, Tokyo (JP); Takahiro Jingu, Tokyo (JP); Akira Hamamatsu, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/088,673

(22) Filed: Apr. 1, 2016

(65) Prior Publication Data

US 2016/0216217 A1 Jul. 28, 2016

Related U.S. Application Data

(63) Continuation of application No. 14/396,908, filed as application No. PCT/JP2013/062139 on Apr. 24, 2013, now Pat. No. 9,329,136.

(30) Foreign Application Priority Data

Apr. 27, 2012 (JP) .................................. 2012-102819

(51) Int. Cl.
*G01N 21/00* (2006.01)
*G01N 21/95* (2006.01)
(Continued)

(52) U.S. Cl.
CPC ......... *G01N 21/9501* (2013.01); *G01J 1/0474* (2013.01); *G01N 21/956* (2013.01);
(Continued)

(58) Field of Classification Search
CPC .............. G01N 21/9501; G01N 21/956; G01N 2021/8825; G01N 23/225; G01N 21/47; G01N 21/8806; G01N 2021/646; G01N 21/211; G01N 21/636; G01N 21/64; G01N 21/94; G01N 23/2204; G01N 23/2251; G01N 23/227

See application file for complete search history.

(56) References Cited

U.S. PATENT DOCUMENTS 5,251,010 A 10/1993 Maltby, Jr.
6,617,603 B2 9/2003 Ishiguro et al.
(Continued)

FOREIGN PATENT DOCUMENTS

JP 2-223845 A 9/1990
JP 8-304050 A 11/1996
(Continued)

OTHER PUBLICATIONS

U.S. Appl. No. 14/396,908, Jan. 6, 2016 Notice of Allowance.
(Continued)

*Primary Examiner* — Michael P Stafira
(74) *Attorney, Agent, or Firm* — Baker Botts L.L.P.

(57) ABSTRACT

To detect an infinitesimal defect, highly precisely measure the dimensions of the detect, a detect inspection device is configured to comprise: a irradiation unit which irradiate light in a linear region on a surface of a sample; a detection unit which detect light from the linear region; and a signal processing unit which processes a signal obtained by detecting light and detecting a defect. The detection unit includes: an optical assembly which diffuses the light from the sample in one direction and forms an image in a direction orthogonal to the one direction; and a detection assembly having an array sensor in which detection pixels are positioned two-dimensionally, which detects the light diffused in the one direction and imaged in the direction orthogonal to the one direction, adds output signals of each of the detection pixels
(Continued)

aligned in the direction in which the light is diffused, and outputs same.

16 Claims, 17 Drawing Sheets

(51) Int. Cl.
*G01N 21/956* (2006.01)
*G01J 1/04* (2006.01)

(52) U.S. Cl.
CPC .......... *G01N 2201/068* (2013.01); *G01N 2201/0697* (2013.01); *G01N 2201/06113* (2013.01); *G01N 2201/12* (2013.01)

(56) References Cited

U.S. PATENT DOCUMENTS

| | | |
|---|---|---|
| 2004/0156043 A1 | 8/2004 | Toker et al. |
| 2006/0215264 A1 | 9/2006 | Birk et al. |
| 2008/0304055 A1 | 12/2008 | Oshima et al. |
| 2009/0279081 A1 | 11/2009 | Urano et al. |
| 2011/0149275 A1 | 6/2011 | Nakano et al. |
| 2015/0146200 A1 | 5/2015 | Honda et al. |

FOREIGN PATENT DOCUMENTS

| | | |
|---|---|---|
| JP | 2001-153640 A | 6/2001 |
| JP | 2001-156425 A | 6/2001 |
| JP | 2007-501934 A | 2/2007 |
| JP | 2008-268140 A | 11/2008 |
| JP | 2011-2314 A | 1/2011 |
| JP | 4698766 B2 | 3/2011 |
| JP | 2012-32252 A | 2/2012 |
| JP | 2012-98103 A | 5/2012 |

OTHER PUBLICATIONS

U.S. Appl. No. 14/396,908, Dec. 4, 2015 Response to Non-Final Office Action.
U.S. Appl. No. 14/396,908, Sep. 17, 2015 Non-Final Office Action.

NO BRANCHING AND
NO SYNTHESIS OF OPTICAL PATH

OPTICAL PATH IS BRANCHED
AND SYNTHESIZED

US 9,568,439 B2

DEFECT INSPECTION DEVICE AND DEFECT INSPECTION METHOD

CLAIM FOR PRIORITY

This application is a continuation of application Ser. No. 14/396,908, filed on Oct. 24, 2014, which is a 371 National Stage of PCT/JP2013/062139 filed on Apr. 24, 2013, the disclosures of which are incorporated in their entirety herein by reference into this application. This application also claims priority from Japanese Patent Application No. 2012-102819 filed on Apr. 27, 2012, the disclosure of which is incorporated in its entirety herein by reference into this application.

BACKGROUND

The present invention relates to a defect inspection method and a defect inspection device where an infinitesimal defect that exists on a surface of a sample is inspected, a position, a type and dimensions of the defect are determined, and a result of the determination is output.

To maintain and enhance the yield of a product in a manufacturing line for a semiconductor substrate, a thin film substrate and others, the inspection of a defect that exists on a surface of the semiconductor substrate, the thin film substrate and others is performed. For prior art for the defect inspection, technique disclosed in Japanese Unexamined Patent Application Publication No. Hei 8-304050 (Patent Literature 1), Japanese Unexamined Patent Application Publication No. 2008-268140 (Patent Literature 2) and others is known.

In Patent Literature 1, it is described that detection sensitivity is enhanced by illuminating the same defect plural times in one inspection by an illumination optical system that linearly illuminates and a detection optical system that divides and detects an illuminated region on a line sensor and adding their scattered light.

In Patent Literature 2, it is described that 2n pieces of APDs corresponding to a laser beam band are linearly arrayed, appropriate two of 2n pieces are combined, the difference between output signals of the two APDs in each combination is calculated, noise by reflected light is eliminated, and a defective pulse for scattered light is output.

CITATION LIST

Patent Literature

Patent literature 1: Japanese Unexamined Patent Application Publication No. Hei 8-304050
Patent Literature 2: Japanese Unexamined Patent Application Publication No. 2008-268140

SUMMARY

For defect inspection used in a manufacturing process of a semiconductor product and others, it is demanded that an infinitesimal defect is detected, the dimensions of the detected defect are precisely measured, a sample is inspected without destroying it (for example, without converting the property of the sample), fixed inspection results are substantially acquired with regard to the number, positions, dimensions and types of detected defects for example when the same sample is inspected and multiple samples are inspected within fixed time.

In the techniques disclosed in Patent Literature 1 and Patent Literature 2, particularly as to an infinitesimal defect having the dimensions of 20 nm or less for example, scattered light caused from the defect is extremely feeble and since a defect signal gets lost in noise by scattered light caused on a surface of a sample, noise from a detector or noise form a detection circuit, the infinitesimal defect cannot be detected. Or when power for illumination is increased to avoid the situation, the temperature of the sample rises by illumination light and the temperature damages the sample. Or when a scanning rate of the sample is reduced to avoid the situation, the area which can be inspected within fixed time of the sample or the number of samples decreases. It has been difficult to detect an infinitesimal defect at high speed as described above.

For a method of detecting feeble light, a photon counting method is known. Generally, a high-sensitivity, high-precision and stable signal is acquired by counting the number of detected photons for feeble light because S-N ratio of the signal is enhanced. For one example of the photon counting method, a method of counting the generated number of pulsed current generated by the incidence of a photon on a photomultiplier and an avalanche photodiode is known. However, since frequencies cannot be counted when plural photons are incident in short time and pulsed current is generated plural times because the speed of a response is slow, the quantity of light cannot be precisely measured and the photon counting method cannot be applied to defect inspection.

Besides, for one example of another photon counting method, a method of measuring the sum of pulsed current generated by the incidence of a photon on each pixel by a detector configured by arraying multiple avalanche photodiode pixels is known. This detector is called a silicon photomultiplier (Si-PM), a pixelated photon detector (PPD) or a multi-pixel photon counter (MPPC). According to this method, unlike photon counting using the single photomultiplier and the avalanche photodiode, since the speed of a response is fast, the quantity of light can be measured even if plural photons are incident in short time. However, since the detector in which multiple avalanche diodes are arrayed is operated as a detector having one "pixel", this method cannot be applied to high-speed or high-sensitivity defect inspection depending upon the parallel detection of plural pixels.

To settle the abovementioned problems, in the present invention is a defect inspection method comprising: irradiating light in a linear region on a surface of the sample; detecting light which is reflected and scattered from the linear region on the sample where the light is irradiated; processing a signal acquired by detecting the reflected and scattered light; and detecting a defect on the sample on the basis of the result of the processing, wherein in step of detecting includes; diffusing the reflected and scattered light from the sample in one direction and imaging the light in a direction perpendicular to the one direction; detecting the reflected and scattered light diffused in one direction and imaged in the direction perpendicular to the one direction by an array sensor on which detection pixels are arranged two-dimensionally; adding an output signal from each detection pixel arranged in a direction in which the reflected and scattered light is diffused out of output signals from the array sensor where the detection pixels for detecting the reflected and scattered light are arranged two-dimensionally; and sequentially extracting a signal acquired by adding the output signals from each detection pixel arranged in the direction in which the reflected and scattered light is diffused in one direction for imaging and processing the signals.

Besides, to achieve the abovementioned object, a defect inspection device includes: irradiation unit which irradiates illumination light on a surface of a sample to be a linear region; detection unit which detects light which is reflected and scattered from the linear region on the sample on which the light is irradiated by the irradiation unit; and signal processing unit which processes a signal acquired by detecting the reflected and scattered light and detects a defect on the sample, wherein the detection unit is provided with; an optical system that diffuses, in one direction, light which is reflected and scattered from the sample and images the light in a direction perpendicular to the one direction; and a detection system that is provided with an array sensor where detection pixels are arrayed two-dimensionally, detects the reflected and scattered light diffused in one direction by the optical system and imaged in the direction perpendicular to the one direction, and adds and outputs an output signal of each detection pixel arranged in the direction in which the reflected and scattered light is diffused.

According to the present invention, the defect inspection device and the inspection method can be provided where the whole surface of the sample can be scanned in a short time, an infinitesimal defect can be detected, reducing thermal damage to the sample, the dimensions of the detected defect can be precisely calculated and a stable result of the inspection can be output.

The problems, the configuration and the effect except the abovementioned ones will be clarified by the description of the following embodiments.

DESCRIPTION OF THE PREFERRED EMBODIMENTS

Figure 1A:
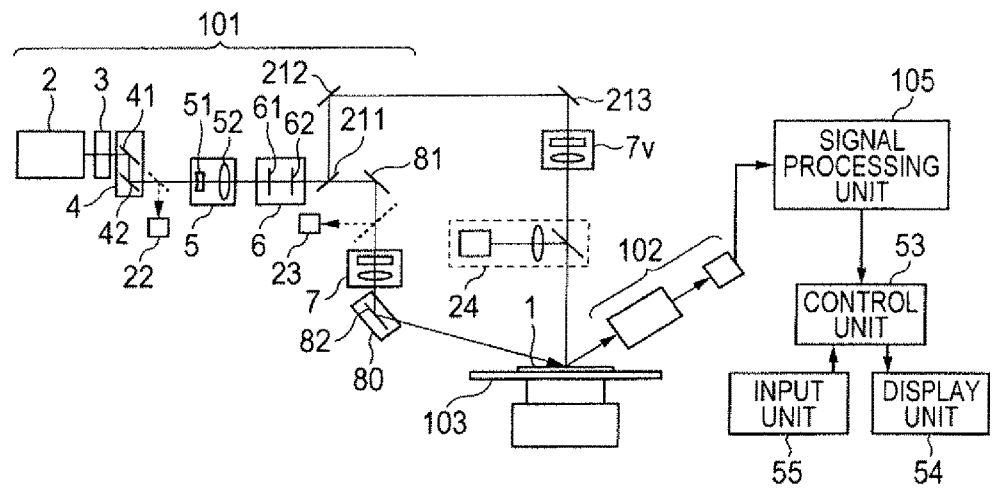
FIG. 1A is a block diagram showing the whole schematic configuration of a defect inspection device equivalent to a first embodiment of the present invention.

The present invention relates to a defect inspection device that enables enhancing defect defection sensitivity, enlarging a range of detectable defects (a dynamic range) and detecting the defects at higher speed. Referring to the drawings, embodiments of the present invention will be described below.

First Embodiment

FIG. 1A shows an example of the schematic configuration of a defect inspection device equivalent to this embodiment. The defect inspection device is properly provided with a illumination unit 101, a detection unit 102, a stage unit 103 on which a sample W can be mounted, a signal processing unit 105, a control unit 53, a display unit 54 and an input unit 55. The illumination unit 101 is properly provided with a laser source 2, an attenuator 3, an outgoing beam adjuster 4, a beam expander 5, a polarization controller 6 and an illumination intensity distribution controller 7.

A laser beam emitted from the laser source 2 is adjusted to desired beam intensity in the attenuator 3, the laser beam is adjusted in a desired beam direction and in a beam traveling direction in the outgoing beam adjuster 4, the laser beam is adjusted to a desired beam diameter in the beam expander 5, the laser beam is adjusted to a desired polarized state in the polarization controller 6, the laser beam is adjusted to desired intensity distribution in the illumination intensity distribution controller 7, and the laser beam is irradiated onto an inspection object region of a sample 1.

An angle of incidence (an angle of inclination to a normal of the surface of the sample) of illumination light to the surface of the sample 1 is determined by positions and angles of reflecting mirrors 81, 82 arranged on an optical path of the illumination unit 101. The incidence angle of the illumination light is set to an angle suitable for detecting an infinitesimal defect. The larger incidence angle is suitable for detecting infinitesimal defects because the larger the incidence angle of the illumination light is, that is, the smaller an elevation angle of the illumination light (an angle between the surface of the sample and an optical axis of the illumination light) is, the weaker scattered light from minute irregularities (called haze) of the surface of the sample 1 to be noise is in relation to scattered light from a minute foreign matter on the surface of the sample 1. Therefore, when scattered light from the minute irregularities of the surface of the sample 1 interferes with the detection of an infinitesimal defect, it is desirable that the incidence angle of the illumination light is set to 75 degrees or more (15 degrees or less in terms of the elevation angle).

In the meantime, when the shortage of the quantity of scattered light from a defect interferes with the detection of the infinitesimal defect, it is desirable that the incidence angle of the illumination light is set between 60 degrees and 75 degrees (between 15 degrees and 30 degrees in terms of the elevation angle) because, in oblique incident illumination, the smaller the incidence angle of the illumination light is, the more the absolute quantity of scattered light from a minute foreign matter is. Besides, in oblique incident illumination, scattered light from a defect on the surface of the sample 1 increases, compared with the other polarized light by turning the polarization of illumination light p-polarized light by polarization control in the polarization controller 6 of the illumination unit 101. Moreover, when scattered light from minute irregularities of the surface of the sample 1 interferes with the detection of an infinitesimal defect, scattered light from the minute irregularities of the surface of the sample 1 decreases, compared with the other polarized light by turning the polarization of illumination light s-polarized light.

In addition, if necessary, an optical path of illumination light is changed by inserting a mirror 21 into an optical path shown in FIG. 1A of the illumination unit 101 by driving means not shown, the illumination light is sequentially reflected on mirrors 212, 213, and the illumination light is irradiated from a direction substantially perpendicular to the surface of the sample (vertical illumination). At this time, illumination intensity distribution on the surface of the sample 1 is controlled as in a case of oblique incident illumination by an illumination intensity distribution controller 7v. To acquire scattered light from a concave defect (a flaw by polishing and a crystal defect due to crystal materials) on the surface of the sample in oblique incident illumination by inserting a beam splitter in the same position as the mirror 21, vertical illumination in which illumination light is irradiated substantially perpendicularly to the surface of the sample 1 is suitable. An illumination intensity distribution monitor 24 shown in FIG. 1A will be described in detail later.

For the laser source 2, the one that oscillates an ultraviolet or vacuum ultraviolet laser beam having a short wavelength (355 nm or less) as a wavelength difficult to penetrate the inside of the sample 1 and outputs the laser beam of 2 W or more is used for detecting an infinitesimal defect in the vicinity of the surface of the sample 1. A diameter of an outgoing beam is approximately 1 mm. To detect a defect inside the sample 1, a laser source that oscillates a visible or infrared laser beam as a wavelength easy to penetrate the inside of the sample 1 is used.

Figure 1B:
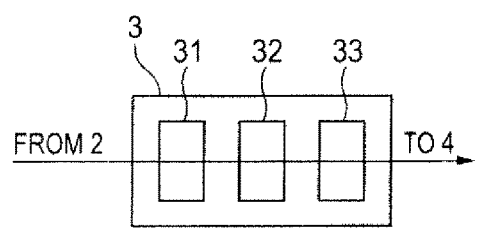
FIG. 1B is a block diagram showing the configuration of the defect inspection device equivalent to the first embodiment of the present invention.

The attenuator 3 is properly provided with a first polarizing plate 31, a half-wave plate 32 rotatable around the optical axis of illumination light and a second polarizing plate 33 as shown in FIG. 1B. Light incident on the attenuator 3 is converted to linearly polarized light by the first polarizing plate 31, a direction of polarization is turned to an arbitrary direction according to an azimuth of a phase lag axis of the half-wave plate 32, and the light passes the second polarizing plate 33. Optical intensity is extinguished at arbitrary ratio by controlling the azimuth of the half-wave plate 32. When a degree of linear polarization of light incident on the attenuator 3 is fully high, the first polarizing plate 31 is not necessarily required. For the attenuator 3, the one in which relation between an input signal and a rate of extinction is calibrated beforehand is used. For the attenuator 3, it is possible both to use an ND filter having gradated density distribution and to use plural ND filters having mutually different density by switching.

The outgoing beam adjuster 4 is provided with plural reflecting mirrors 41, 42. In this case, an embodiment when the outgoing beam adjuster is configured by the two reflecting mirrors 41, 42 will be described below. However, the present invention is not limited to this, and three or more reflecting mirrors may also be properly used. In this case, a three-dimensional rectangular coordinate system (XYZ coordinates) is temporarily defined and it is supposed that incident light on the reflecting mirror shall travel in a +X direction. The first reflecting mirror 41 is installed so that incident light is deflected in a +Y direction (which means the incidence and reflection of light occurs in an XY plane) and the second reflecting mirror 42 is installed so that the light reflected on the first reflecting mirror 41 is deflected in a +Z direction (which means the incidence and reflection of light occurs in a YZ plane). A position and a traveling direction (an angle) of light outgoing from the outgoing beam adjuster 4 are adjusted by the parallel displacement and the adjustment of a shift angle of each reflecting mirror 41, 42. The adjustment of a position and an angle on an XZ plane and the adjustment of a position and an angle on the YZ plane respectively of light (traveling in the +Z direction) outgoing from the outgoing beam adjuster 4 can be independently performed by arranging so that the incidence and reflection surface (the XY plane) of the first reflecting mirror 41 and the incidence and reflection surface (the YZ plane) of the second reflecting mirror 42 are perpendicular as described above.

The beam expander 5 is provided with two or more groups of lenses 51, 52 and has a function to magnify a diameter of an incident parallel beam. For example, a Galilean beam expander provided with the combination of a concave lens and a convex lens is used. The beam expander 5 is installed on a translational stage, not shown, having two axes or more and the adjustment of the position is possible so that a predetermined beam position and the center are coincident. Besides, the beam expander 5 is provided with a function to adjust a shift angle of the whole beam expander 5 so that an optical axis of the beam expander 5 and a predetermined beam optical axis are coincident. The magnification of a diameter of a beam can be controlled by adjusting an interval between the groups of lenses 51, 52 (a zoom mechanism). When light incident on the beam expander 5 is not parallel, the magnification of the diameter of the beam and collimation (the semi-parallelization of a luminous flux) are simultaneously performed by adjusting the interval between the groups of lenses 51, 52. A luminous flux may also be collimated by installing a collimator lens on the upstream side of the beam expander 5 independently of the beam expander 5. The magnification of a beam diameter by the beam expander 5 is approximately 5 to 10 times and a beam outgoing from the light source and having a diameter of 1 mm is magnified to be approximately 5 to 10 mm.

The polarization controller 6 is configured by a half-wave plate 61 and a quarter-wave plate 62 and controls a polarized state of illumination light to be an arbitrary polarized state. On the way of the optical path of the illumination unit 101, a state of light incident on the beam expander 5 and a state of light incident on the illumination intensity distribution controller 7 are measured by a beam monitor 22.

Reference numerals 22, 23 denote a beam monitor and the beam monitors monitor the intensity and a position of a laser beam on the optical axis.

FIGS. 2 to 6 schematically show positional relation between an illumination optical axis 120 led onto the sample surface by the illumination unit 101 and an illumination intensity distribution pattern. It should be noted, the configuration shown in FIGS. 2 to 6 of the illumination unit 101 shows apart of the configuration of the illumination unit 101, and the outgoing beam adjuster 4, a mirror 211, the beam monitors 22, 23 and others are omitted here.

Figure 2:
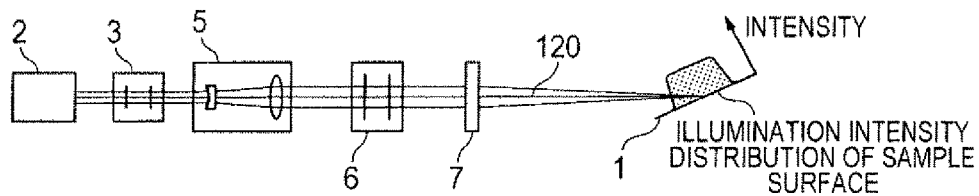
FIG. 2 is a block diagram showing a first example of the configuration of a illumination unit for acquiring an illumination intensity distribution pattern realized by the illumination unit of the defect inspection device equivalent to the first embodiment of the present invention.

FIG. 2 schematically shows the section of an incidence plane (a plane including the optical axis of illumination and the normal of the surface of the sample 1) of oblique incident illustration. Oblique incident illumination tilts to the surface of the sample 1 on the incidence plane. Substantially uniform illumination intensity distribution is made on the incidence plane by the illumination unit 101. As shown in an illumination intensity distribution schematic diagram on the right side of FIG. 2, the length of a part in which illumination intensity is even in a linearly illuminated region is set to approximately 100 μm to 4 mm so as to inspect large area per unit time.

Figure 3:
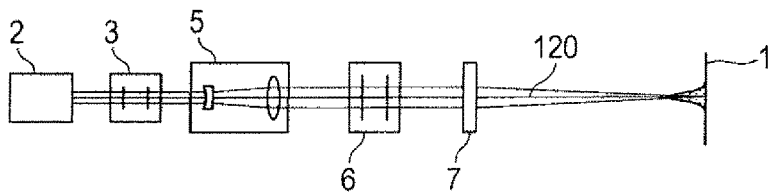
FIG. 3 is a block diagram showing a second example of the configuration of the illumination unit for acquiring an illumination intensity distribution pattern realized by the illumination unit of the defect inspection device equivalent to the first embodiment of the present invention.

FIG. 3 schematically shows the section of a plane including the normal of the surface of the sample 1 and perpendicular to the incidence plane of the oblique incident illumination. On this plane, illumination intensity distribution on the surface of the sample 1 is illumination intensity distribution in which the intensity of the periphery is weaker, compared with that of the center. More concretely, the illumination intensity distribution is Gaussian distribution that reflects the intensity distribution of light incident on the illumination intensity distribution controller 7, or a primary Bessel function of the first kind that reflects a shape of an opening of the illumination intensity distribution controller 7 or intensity distribution similar to sinc function. The length of illumination intensity distribution (the length of a region having the illumination intensity of the maximum illumination intensity of 13.5% or more) on this plane is shorter than the length of the part in which illumination intensity on the incidence plane is even and is set to approximately 2.5 to 20 μm so as to reduce haze caused from the surface of the sample 1. The illumination intensity distribution controller 7 is provided with optical elements including an aspherical lens, a diffractive optical element, a cylindrical lens array and a light pipe respectively described later. The optical elements that configure the illumination intensity distribution controller 7 are installed perpendicularly to the illumination optical axis 120 as shown in FIGS. 2 and 3.

Figure 4:
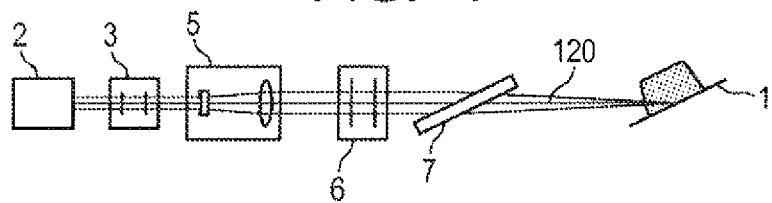
FIG. 4 is a block diagram showing a third example of the configuration of the illumination unit for acquiring an illumination intensity distribution pattern realized by the illumination unit of the defect inspection device equivalent to the first embodiment of the present invention.

FIG. 4 shows a configuration in which the illumination intensity distribution controller 7 is installed in parallel to the surface of the sample 1, compared with the configuration shown in FIG. 2. In this case, the illumination intensity distribution controller 7 is installed with the controller tilted to the illumination optical axis 120.

Figure 5:
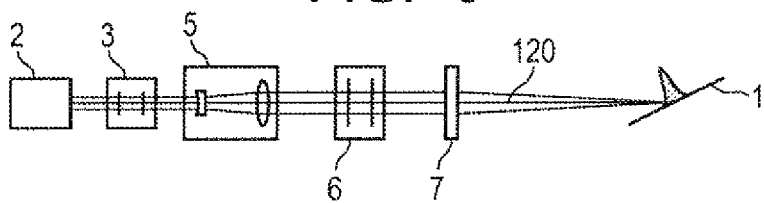
FIG. 5 is a block diagram showing a fourth example of the configuration of the illumination unit for acquiring an illumination intensity distribution pattern realized by the illumination unit of the defect inspection device equivalent to the first embodiment of the present invention.
Figure 6:
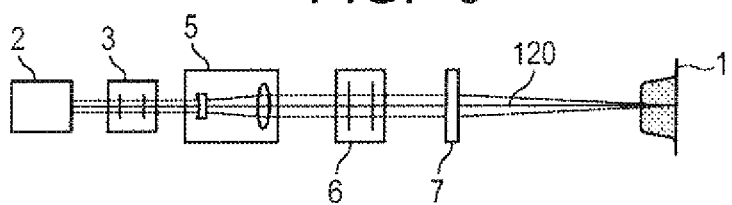
FIG. 6 is a block diagram showing a fifth example of the configuration of the illumination unit for acquiring an illumination intensity distribution pattern realized by the illumination unit of the defect inspection device equivalent to the first embodiment of the present invention.

Besides, each configuration shown in FIGS. 5 and 6 shows a configuration when the tilt to the surface of the sample 1 of the illumination optical axis 120 is changed in the configurations shown in FIGS. 3 and 2. That is, each configuration shown in FIGS. 5 and 6 shows a state when the orientation of the linearly illuminated region on the sample 1 to a direction in which the illumination optical axis 120 is incident on the surface of the sample 1 is changed by 90 degrees with the cases described in reference to FIGS. 2 and 3.

The configuration shown in FIG. 5 schematically shows the section of the incidence plane (the plane including the illumination optical axis and the normal of the surface of the sample 1) of oblique incident illumination and the oblique incident illumination is tilted to the surface of the sample 1 on the incidence plane. On this plane, illumination intensity distribution on the surface of the sample 1 is illumination intensity distribution in which the intensity of the periphery is weaker comparing to that of the center. In the meantime, the configuration shown in FIG. 6 schematically shows the section of a plane including the normal of the surface of the sample 1 and perpendicular to the incidence plane of oblique incident illumination. On the incidence plane, substantially uniform illumination intensity distribution is formed.

Figure 7:
FIG. 7 is a side view showing one example of an optical element with which an illumination intensity distribution controller of the defect inspection device equivalent to the first embodiment of the present invention is provided.

The illumination intensity distribution controller 7 is provided with the optical elements that act on the phase distribution and the intensity distribution of incident light. For the optical element that configures the illumination intensity distribution controller 7, the diffractive optical element (DOE) 71 is used (see FIG. 7). The diffractive optical element 71 is acquired by forming a minute undulating shape having the similar dimension or smaller to/than a wavelength of light on a surface of a substrate made of materials that transmit incident light. For the material that transmits incident light, fused quartz is used in case an ultraviolet light is used for the illumination.

To inhibit the attenuation of light transmitted in the diffractive optical element 71, it is desirable to use a diffractive optical element to which reflection reducing coating is applied. For the formation of the minute undulating shape, lithography process is applied. Illumination intensity distribution on the surface of the sample according to the undulating shape of the diffractive optical element 71 is formed by passing a quasi-parallel light, which is formed by the light passing through the beam expander 5, through the diffractive optical element 71. The undulating shape of the diffractive optical element 71 is produced by designing to be a shape acquired based upon calculation using Fourier optical theory so that illumination intensity distribution formed on the surface of the sample has long even distribution on the incidence plane.

The optical elements provided to the illumination intensity distribution controller 7 are provided with a translation adjustment mechanism having two axes or more and a turn adjustment mechanism having two axes or more so that a relative position and an angle with an optical axis of incident light can be adjusted. Further, a focus adjustment mechanism based upon a motion in a direction of the optical axis is provided. For an alternative optical element having the similar function to the diffractive optical element 71, the combination of an aspherical lens, a cylindrical lens array and a cylindrical lens and the combination of a light pipe and an imaging lens may also be used.

Figure 8:
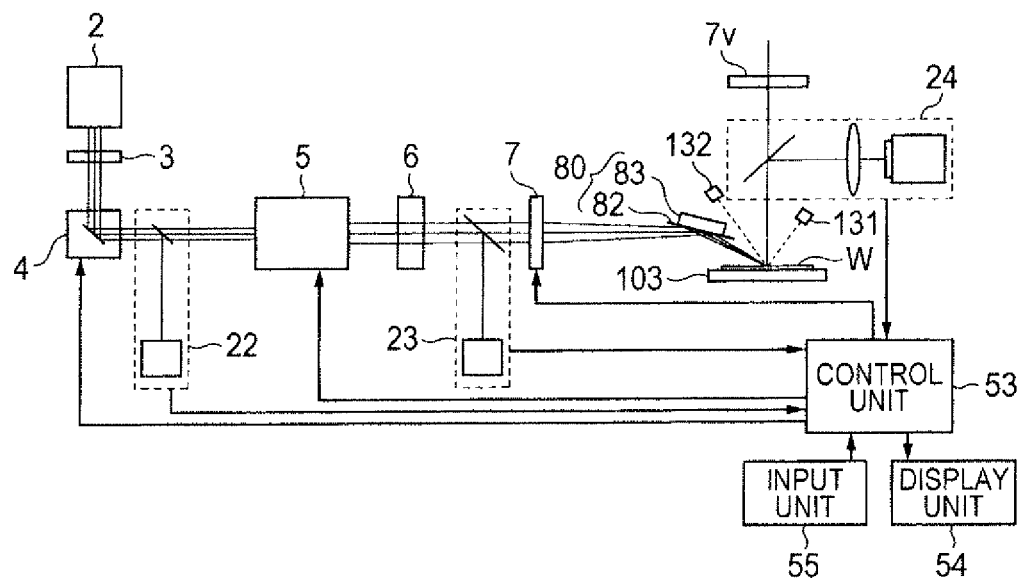
FIG. 8 is a block diagram showing one example of an embodiment of means for measuring a state of illumination light and adjustment means in the illumination unit of the defect inspection device equivalent to the first embodiment of the present invention.

In the configuration shown in FIG. 1, a state of illumination light in the illumination unit 101 is measured by the beam monitor 22. The beam monitor 22 measures a position and an angle (a traveling direction) respectively of illumination light that passes the outgoing beam adjuster 4 or a position and a wave front of illumination light incident on the illumination intensity distribution controller 7 and outputs them. The measurement of the position of illumination light is performed by measuring a position of the center of gravity of the optical intensity of the illumination light. For a concrete position measurement means, a position sensitive detector (PSD) or an image sensor such as a CCD sensor and a CMOS sensor are used. The measurement of an angle of illumination light is performed by the position sensitive detector or the image sensor respectively which is installed in a position farther from the light source than the position measurement means or installed in a position focused by a collimator lens. As shown in FIG. 8, a position and an angle of illumination light measured by the beam monitor 22 are input to the control unit 53 and are displayed on the display unit 54. When the position or the angle of illumination light is off a predetermined position or angle, the outgoing beam adjuster 4 adjusts so that the illumination light is returned to the predetermined position.

The measurement of a wave front of illumination light by the beam monitor 22 is performed to measure a degree of parallelization of light incident on the illumination intensity distribution controller 7. Measurement by a shearing interferometer or measurement by a Shack Hartman wave front sensor is performed.

The shearing interferometer measures a state of diverges or converges of the illumination light by observing a pattern of an interference fringe formed by projecting on a screen both of a reflected light from a front surface of an optical glass and a reflected light from a back surface of the optical glass. In the shearing interferometer, the optical glass is inserted by obliquely tilting in the optical path of illumination light and it has the thickness of approximately several mm and both faces of which are polished flatly. As the shearing interferometer, for an example, SPUV-25 manufactured by SIGMA KOKI can be given. When an image sensor such as a CCD sensor and a CMOS sensor is installed in a position of the screen, the automatic measurement of the state in which illumination light diverges or converges is possible.

The Shack Hartman wave front sensor divides a wave front by the minute lens array, projects the divided ones on an image sensor such as a CCD sensor, and measures the inclination of an individual wave front based upon the displacement of a projected position. Compared with the shearing interferometer, detailed wave front measurement such as the partial disturbance of a wave front is possible by using the Shack Hartman wave front sensor.

When it is ascertained by the wave-front measurement that the light incident on the illumination intensity controller 7 is not a quasi-parallel light but a divergence light or a convergence light, the incident light can be arranged to approach the quasi-parallel light by displacing the lens groups of the beam expander 5 which is installed on the upstream side of the illumination intensity controller 7, in the direction of the optical axis. Besides, when it is ascertained by the wave-front measurement that a wave front of the light incident on the illumination intensity controller 7 is partially tilted, the wave front can be adjusted to be approximately flat by inserting a spatial optical phase modulation element (not shown) which is one type of a spatial light modulator (SLM) on the upstream side of the illumination intensity controller 7 and applying suitable phase difference every position on the section of a luminous flux so that the wave front is flat. That is, illumination light can be made to approximate quasi-parallel light. The wave front precision (displacement from a predetermined wave front (a designed value or an initial state)) of light incident on the illumination intensity distribution controller 7 is inhibited to be $\lambda/10$ rms or less by the abovementioned wave front precision measurement/adjustment means.

Illumination intensity distribution on the sample surface adjusted by the illumination intensity distribution controller 7 is measured by the illumination intensity distribution monitor 24. As shown in FIG. 1, when vertical illumination is used, illumination intensity distribution on the sample surface adjusted by the illumination intensity distribution controller 7v is also similarly measured by the illumination intensity distribution monitor 24. The illumination intensity distribution monitor 24 images the surface of the sample on an image sensor such as a CCD sensor or a CMOS sensor via lenses and detects as an image. An image of illumination intensity distribution detected by the illumination intensity distribution monitor 24 is processed in the control unit 53, a position of the center of gravity of intensity, maximum intensity, a maximum intensity position, the width and the length (the width and the length of an illumination intensity distribution region having predetermined radio or larger to predetermined intensity or more or a maximum intensity value) of the illumination intensity distribution and others are calculated, and they are displayed together with a contour of the illumination intensity distribution and its sectional waveform on the display unit 54.

In the case of oblique incident illumination, the disturbance of illumination intensity distribution by the displacement of a position of the illumination intensity distribution and defocusing is caused by the displacement in height of the sample surface. To inhibit this, the height of the sample surface is measured and when the height varies, the displacement is corrected by the illumination intensity distribution controller 7 or by the adjustment of height in the z-axis of the stage unit 103. The configuration for measuring the height of the sample surface will be described below in reference to FIG. 8.

For the measurement of the height of the sample surface, the light emitting portion 131 and the photodetector 132 that receives light emitted from the light emitting portion 131 and reflected on the sample surface are used. The light emitting portion 131 is provided with a light source such as a semiconductor laser and a projection lens. The photodetector 132 is provided with a light receiving lens and a position sensitive detector. To measure a glossy surface of a sample such as a surface of semiconductor silicon or a surface of a magnetic disk substrate, the light emitting portion 131 and the photodetector 132 are arranged so that light emitted from the light emitting portion 131 and regularly reflected on the sample surface is detected in the photodetector 132. The displacement in height of the sample surface is detected as the displacement of a position of a light spot detected by the position sensitive detector in the photodetector 132 according to a principle of triangulation.

The correction of the displacement in an in-sample plane direction of an illumination light illuminated position due to the displacement in height of the sample surface is performed by deflection angle adjustment by a deflection means 80 installed on the downstream side of the illumination intensity distribution controller 7 to direct illumination light toward the sample surface. The deflection means 80 is provided with a reflecting mirror 82 that deflects illumination light and a piezo-element 83 that controls a tilt angle to an illumination optical axis of the reflecting mirror, and controls the tilt angle at a frequency of 400 Hz or more so that the tilt angle is in a range of approximately ±1 m rad. The quantity of the displacement in the in-sample plane direction of the illumination light irradiated position is acquired based upon a measured value of the displacement of the height and an incidence angle of illumination light, and the reflecting mirror 82 is controlled by the deflection means 80 according to a control signal output from the control unit 53 to correct the displacement. The displacement in the in-sample plane direction of the illumination light irradiated position can also be measured by directly measuring a position of the center of gravity of illumination intensity distribution and others using the illumination intensity distribution monitor 24.

When the displacement in the in-sample plane direction of the illumination light irradiated position due to the displacement in height of the sample surface is corrected by the deflection means 80, the defocusing of the light spot is caused depending upon the quantity of the displacement because optical path length between the illumination intensity distribution controller 7 and the surface of the sample 1 varies from that before the correction. The variation of the optical path length is acquired based upon the measured value of the displacement of the height and the incidence angle of illumination light and the defocusing is reduced by the adjustment of positions in the direction of the optical axis of the optical elements provided to the illumination intensity distribution controller 7 or by the adjustment of an angle of divergence by the beam expander 5 and others based upon the variation of the optical path length.

Figure 10A:
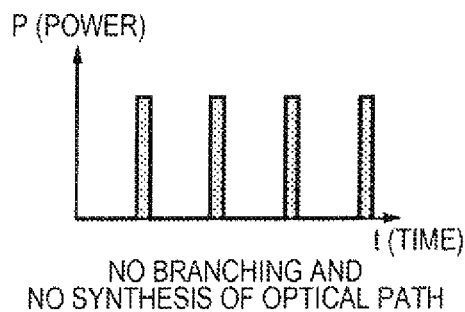
FIG. 10A is a graph showing relation between pulses of a laser beam irradiated on a surface of a sample when no optical path is branched and synthesized in the illumination unit of the defect inspection device equivalent to the first embodiment of the present invention and energy.
Figure 10B:
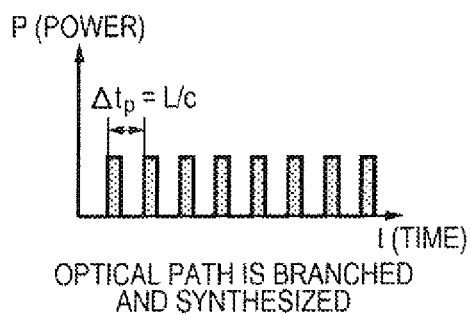
FIG. 10B is a graph showing relation between pulses of a laser beam irradiated on the surface of the sample when an optical path is branched and optical paths are synthesized in the illumination unit of the defect inspection device equivalent to the first embodiment of the present invention and energy.

When a pulse laser that can easily acquire high output is used for the laser source 2, the energy of illumination applied to the sample 1 concentrates in a moment in which a pulse laser is incident as shown in FIG. 10A thermal damage may be caused in the sample 1 due to the momentary rise of temperature by the incidence of the pulse laser. To avoid this, it is effective to reduce energy per pulse, keeping total energy as shown in FIG. 10B by branching an optical path of the pulse laser and synthesizing the optical paths after optical path difference is applied to the branched optical paths.

Figure 9:
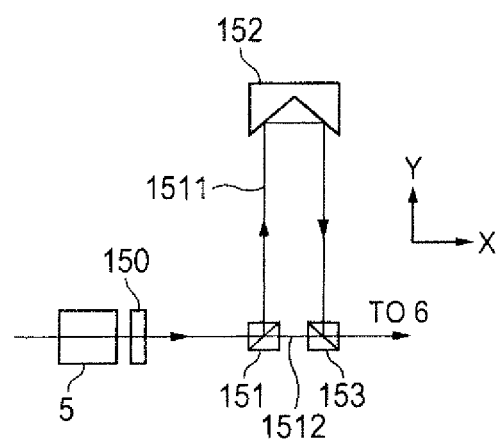
FIG. 9 is a block diagram showing one example of means for reducing energy per single pulse by the branching of an optical path and the synthesis of optical paths in the illumination unit of the defect inspection device equivalent to the first embodiment of the present invention.

FIG. 9 shows one example of an optical system for embodying the abovementioned. Illumination light after passing through the beam expander 5 is branched by the polarizing beam splitter 151 into a first optical path 1511 reflected by a polarizing beam splitter 151 and a second optical path 1512 transmitted through the polarizing beam splitter 151. The illumination light branched on the side of the first optical path 1511 is reflected by a retro-reflector 152, is returned on the side of a polarizing beam splitter 153, and is reflected by the polarizing beam splitter 153. The illumination light branched on the side of the first optical path travels on the same optical path as an optical path of illumination light transmitted through the polarizing beam splitter 151 and branched on the side of the second optical path 1512. Then the branched two illumination lights are synthesized and the synthesized illumination light is incident on the polarization controller 6.

The retro-reflector 152 is provided with two or more reflecting mirrors mutually perpendicular and backs input light in a direction reverse by 180 degrees. The retro-reflector is also called a corner cube. In place of the retro-reflector, independent two or more reflecting mirrors may also be used. To equalize the intensity of light reflected from the polarizing beam splitter 151 and the intensity of light transmitted through it, the illumination light is adjusted to circularly polarized light or linearly polarized light polarized by 45 degrees obliquely and others by a wave plate 150. When optical path difference between the first optical path 1511 and the second optical path 1512 is assumed L, a time interval Δtp between a pulse of light that passes the first optical path and a pulse of light that passes the second optical path is L/c. The momentary rise of temperature of the sample by a single pulse and the rise of temperature due to the storage of heat by plural pulses are inhibited by setting the Δtp so that it is equal or longer to/than time required to soften the rise of temperature when the single pulse is incident.

Figure 11:
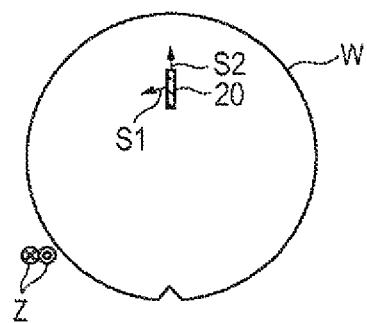
FIG. 11 is a plan view showing a shape of an illuminated region on the surface of the sample by the illumination unit of the defect inspection device equivalent to the first embodiment of the present invention.

A distributional pattern of illuminance (a light spot 20) formed on the surface of the sample 1 by the illumination unit 101 and a sample scanning method will be described below in reference to FIGS. 11 and 12. For the sample W, a circular semiconductor silicon wafer is assumed. The stage unit 103 is provided with a translational stage, a rotating stage and a Z stage for adjusting the height of the surface of the sample 1 (all not shown). The light spot 20 has illumination intensity distribution (linear illumination) long in one direction as described above, its longitudinal direction shall be S2, and a direction (a direction of the width of a line) substantially perpendicular to the longitudinal direction S2 shall be S1. Scanning is performed in the circumferential direction S1 of a circle having a rotation axis of the rotating stage in the center by a rotational motion of the rotating stage and in the translational direction S2 of the translational stage by a translational motion of the translational stage. The light spot draws a spiral locus T on the sample 1 by scanning by distance equal to or shorter than the length in the longitudinal direction of the light spot 20 in the scanning direction S2 while the sample is rotated once by scanning in the scanning direction S1, and the whole surface of the sample 1 is scanned.

Plural detection units 102 are arranged to detect scattered light in plural directions scattered from the light spot 20. Examples of the arrangement of the detection units 102 for the sample W and the light spot 20 will be described in reference to FIGS. 13 to 15 below.

Figure 13:
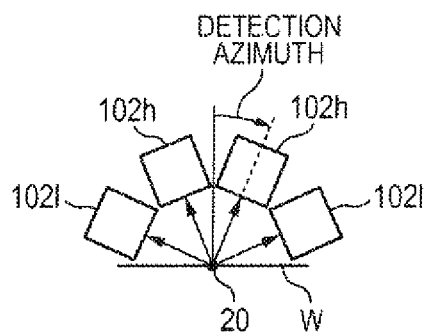
FIG. 13 is a side view showing arrangement and detection directions viewed from the side in a detection unit of the defect inspection device equivalent to the first embodiment of the present invention.

FIG. 13 is a side view showing the arrangement of the detection units 102. An angle between the normal of the sample 1 and a detection direction (a central direction of an opening for detection) by the detection unit 102 is defined as a detection zenithal angle. The detection unit 102 is configured by properly using a high-angle detector 102h with its detection zenithal angle of 45 degrees or less and a low-angle detector 102l with its detection zenithal angle of 45 degrees or more. Plural high-angle detectors 102h and plural low-angle detectors 102l are provided so that scattered light scattered in many directions is covered at each detection zenithal angle.

Figure 14:
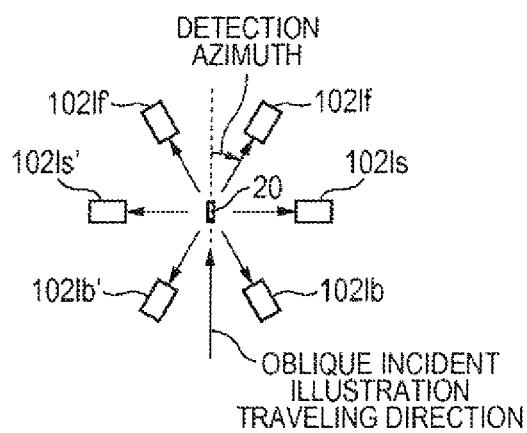
FIG. 14 is a plan view showing the arrangement and detection directions of low-angle detectors of the defect inspection device equivalent to the first embodiment of the present invention.

FIG. 14 is a plan view showing the arrangement of the low-angle detectors 102l. An angle between a traveling direction of oblique incident illumination and the detection direction on a plane parallel to the surface of the sample W is defined as a detection azimuth. The low-angle detector 102l is properly provided with a low-angle front detector 102lf, a low-angle side detector 102ls, a low-angle back detector 102lb, and a low-angle front detector 102lf', a low-angle side detector 102ls' a low-angle back detector 102lb' which are respectively located in symmetrical positions with former in relation to an illumination incidence plane. For example, the low-angle front detector 102lf is installed so that its detection azimuth is between 0 degree and 60 degrees, the low-angle side detector 102ls is installed so that its detection azimuth is between 60 degrees and 120 degrees, and the low-angle back detector 102lb is installed so that its detection azimuth is between 120 degrees and 180 degrees.

Figure 15:
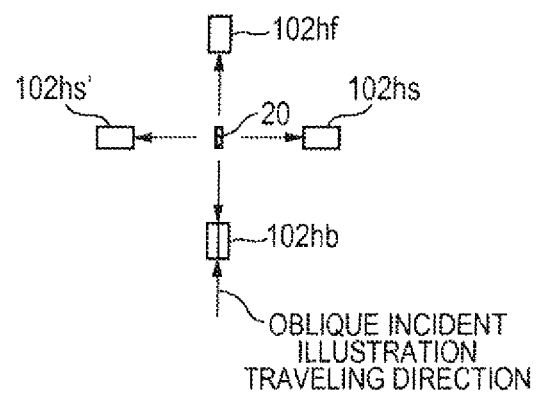
FIG. 15 is a plan view showing the arrangement and detection directions of high-angle detectors of the defect inspection device equivalent to the first embodiment of the present invention.

FIG. 15 is a plan view showing the arrangement of the high-angle detector 102h. The high-angle detector 102h is properly provided with a high-angle front detector 102hf, a high-angle side detector 102hs, a high-angle back detector 102hb and a high-angle side detector 102hs' located in a symmetrical position with the high-angle side detector 102*hs* in relation to the illumination incidence plane. For example, the high-angle front detector 102*hf* is installed so that its detection azimuth is between 0 degree and 45 degrees, the high-angle side detector 102*hs* is installed so that its detection azimuth is between 45 degrees and 135 degrees, and the high-angle back detector 102*hb* is installed so that its detection azimuth is between 135 degrees and 180 degrees. A case where the four high-angle detectors 102*h* are provided and the six low-angle detectors 102*l* are provided is described above; however, the present invention is not limited to this case, and the number and positions of the detectors may also be properly changed.

Figure 16:
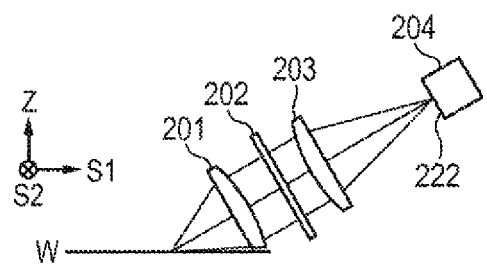
FIG. 16 is a block diagram showing the configuration of each detector 102*ls*, 102*ls'* installed at a low angle, 102*hs*, 102*hs'* installed at a high angle respectively having a detection azimuth of 90 degrees in the defect inspection device equivalent to the first embodiment of the present invention.

FIG. 16 shows an example of the concrete configuration of the detection unit 102. Scattered light generated from the light spot 20 is converged by an objective lens 201, then it is led to a detection system 204 provided with a plural-pixel sensor by an imaging lens 203 after passing through a polarization filter 202, and an image of the scattered light from the light spot 20 is detected by the detection system 204 provided with the plural-pixel sensor having a configuration described later. To efficiently detect the scattered light, it is desirable that the numerical aperture (NA) for detection of the objective lens 201 is 0.3 or more. In the case of the low-angle detector, a lower end of the objective lens is cut if necessary so that the interference of the lower end of the objective lens 201 with the sample W is avoided. The polarization filter 202 is configured by a polarizing plate or a polarizing beam splitter and is installed so that a linearly polarized component in an arbitrary direction is cut. For the polarizing plate, a wire grating polarizing plate or a polarizing beam splitter the transmittance of which is respectively 80% or more is used. When an arbitrary polarized component including elliptical polarization is cut, the polarization filter 202 configured by a wave plate and a polarizing plate is installed.

The detection unit 102 shown in FIG. 16 is an effective configuration in the detectors 102*ls*, 102*ls*', 102*hs* and 102*hs*' respectively arranged in a direction perpendicular to the longitudinal direction (the side) of the linear light spot 20 of the sample 1 shown in FIGS. 14 and 15. However, in the case of the detectors 102*lb*, 102*lb*', 102*lf*, 102*lf*', 102*hf* and 102*hb* installed in oblique directions to the longitudinal direction of the light spot 20, that is, in front of or at the back of the light spot 20, as distance from each position in the longitudinal direction of the light spot 20 to the objective lens 201 is different, an image of scattered light from the light spot 20 cannot be formed in the detection system 204. Then, the configuration of the detection unit 102 in each detector installed in the oblique direction to the longitudinal direction of the light spot 20 of which an image of scattered light from the light spot 20 can be formed in the detection system 204 will be described in reference to FIG. 17 below.

Figure 17:
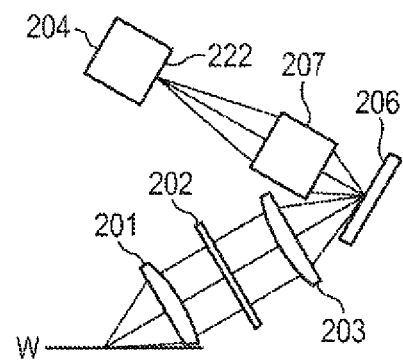
FIG. 17 is a block diagram showing the configuration of each detector 102*lf*, 102*lf'* installed in front at a low angle, 102*lb*, 102*lb'* installed at the back at the low angle, 102*hf* installed in front at a high angle, 102*hb* installed at the back at the high angle in the defect inspection device equivalent to the first embodiment of the present invention.

The configuration of the objective lens 201, the polarization filter 202 and the imaging lens 203 in the configuration of the detection unit 102 shown in FIG. 17 is the same as the configuration described in reference to FIG. 16. In the detection unit 102 shown in FIG. 17, a diffraction grating 206 and an imaging system 207 are provided at the back of the imaging lens 203 to enable forming an image of scattered light from the light spot 20 in the detection system 204.

Scattered light generated from the light spot 20 is converged by the objective lens 201 and after the converged scattered light passing through the polarization filter 202, an image (an intermediate image) of the sample surface is imaged on the diffraction grating 206 installed on a plane conjugate with the sample surface by the imaging lens 203.

The image of the sample surface formed on the diffraction grating 206 is projected and detected on light receiving surfaces of the plural-pixel sensor 204 by the imaging system 207. The plural-pixel sensor 204 is installed on the conjugate plane with the sample surface so that a direction of the array of pixels is coincident with a longitudinal direction of an image of the light spot 20 in accordance with a shape of the light spot 20 long in one direction. The diffraction grating 206 is installed to diffract the light led by the imaging lens 203 for forming the immediate image in the direction of the normal of the surface of the diffraction grating 206. And the shape of the grating of the diffraction grating 206 is formed so that N"th" diffracted light of incident light along an optical axis of light led by the imaging lens 203 for forming the intermediate image travels in a direction of a normal of a surface of the diffraction grating 206. To enhance diffraction efficiency, a blazed diffraction grating is used.

The displacement of a focus is also reduced in the direction S1 on the sample surface by adopting the above-mentioned configuration and installing the plural-pixel sensor 204 on the conjugate plane with the sample surface, an effective field of view can be secured in a large range, and scattered light can be detected with the reduced loss of the light quantity.

Figure 18:
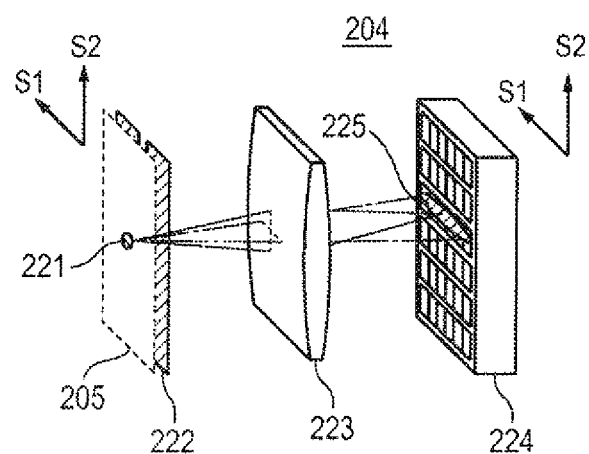
FIG. 18 is a perspective view showing a first example of a detection system provided with a plural-pixel sensor in the detection unit of the defect inspection device equivalent to the first embodiment of the present invention.

FIG. 18 shows the configuration of the detection system 204 provided with the plural-pixel sensor. An image of the sample surface is imaged on a conjugate plane 205 which is conjugate with the sample surface by the objective lens 201 and the imaging lens 203 in the configuration shown in FIG. 16. The detection system 204 shown in FIG. 18 and provided with the plural-pixel sensor is equipped with a slit plate 222, an uniaxial imaging system 223 and an array sensor 224. The slit plate 222 is installed on the conjugate plane 205. A defect image 221 and an uniaxial enlarged image 225 of the defect image respectively in FIG. 18 schematically show one example that a defect is located in the center of a detection field of view of the detection unit 102. After the defect image 221 is once imaged on the conjugate plane 205, the defect image travels in a direction of an optical axis of the detection unit 102 with an angle of divergence according to NA on the side of the image of the imaging lens 203. An image is formed from this light in a direction corresponding to the scanning direction S2 on the conjugate plane 205 by the uniaxial imaging system 223 and images on a light receiving surface of the array sensor 224. On the other hand, in a direction corresponding to the scanning direction S1 on the conjugate plane 205, the light reaches the light receiving surface of the array sensor 224 in a state with the angle of divergence.

The uniaxial imaging system 223 has a function that focuses light only in the direction corresponding to the scanning direction S1 and is configured by a cylindrical lens or the combination of the cylindrical lens and a spherical lens. The defect image 221 is enlarged in the direction corresponding to the scanning direction S1 by the action of the uniaxial imaging system 223. The size of the defect image on the conjugate plane 205 is determined by the optical resolution of the detection unit 102 in the case that an infinitesimal detect is smaller than a wavelength of illumination light, and concretely, the size is determined by the NA on the side of the image of the imaging lens 203 (size of image of infinitesimal detect (spread of spot image) =1.22×(wavelength)/(NA on image side)). The length in the direction S1 of the uniaxial enlarged image 225 of the defect image, that is, magnification in the direction S1 is determined by optical path length between the conjugate plane 205 and the light receiving surface of the array sensor 224 and the NA on the side of the image of the imaging lens 203. The detection system 204 provided with the plural-pixel sensor is configured so that this length is substantially equal to the length in the direction S1 of the light receiving surface of the array sensor 224. The width in the direction S2 of the uniaxial enlarged image 225 of the defect image is determined by the magnification of the uniaxial imaging system 223. The detection system 204 provided with the plural-pixel sensor is configured so that this length is similar to the length in the direction S2 of the light receiving surface of the array sensor 224 or shorter.

Scattered light from the sample surface is produced from a position on which the light spot 20 is irradiated and is detected by the detection unit 102. However, illumination light of relatively weak intensity also substantially irradiates a region outside the light spot 20 by an undulation property of light. As a result, some of scattered light produced by a large foreign matter or at a corner of an end of the sample surface outside the light spot 20 is incident on the light receiving surface of the array sensor 224 and may deteriorate sensitivity as noise. When this comes into question, this obstructive scattered light is excluded by installing the shielding slit plate 222 and the noise is reduced. The shielding slit is provided with a slit-shaped opening (a light transmitted part) having width wider than the width of the image of the light spot 20 formed on the conjugate plane 205 and is installed so that the center of the slit-shaped opening is coincident with a position of the image of the light spot 20. As a part except the opening is shielded, scattered light from the part except a region in which the light spot 20 is located on the sample surface is reduced.

Figure 19:
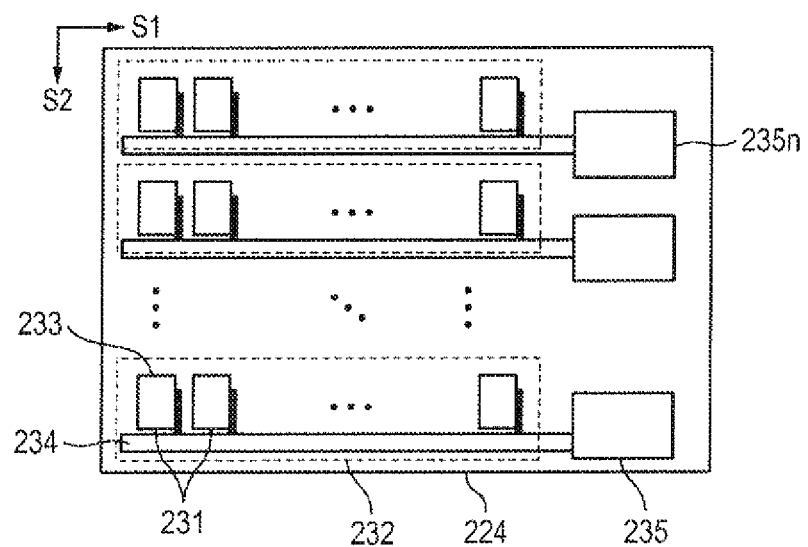
FIG. 19 is a front view showing a first example of a sensor face of an array sensor of the detection system provided with the plural-pixel sensor in the detection unit in the first embodiment of the present invention.

FIG. 19 shows one example of the configuration of the light receiving surface of the array sensor 224. The array sensor 224 has the configuration in which plural avalanche photodiodes (APD) are arrayed two-dimensionally. A light receiving part of the individual APD will be called an APD pixel below. Voltage is applied to the APD pixel 231 so that each is operated in Geiger mode (multiplication factor of photoelectron: $10^5$ or more). When one photon is incident on the APD pixel 231, a photoelectron is generated in the APD pixel 231 at a probability according to the quantum efficiency of the APD pixel, photoelectrons are multiplied by the action of the Geiger-mode APD, and a pulsed electric signal is output. An APD pixel line 232 (a set of APD pixels encircled by a rectangular dotted line 232 shown in FIG. 19) in a direction shown by an arrow S1 is set as one unit, a pulsed electric signal generated in each APD included in the pixel line is summed via a wiring pattern 234 every APD pixel line in the direction S1, and the pulsed electric signals are output from a pad 235. Plural APD pixel lines are arrayed in a direction shown by an arrow S2 and output signals of APD pixels in each line are output in parallel.

Figure 20:
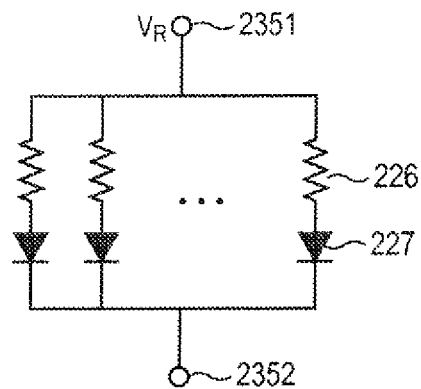
FIG. 20 is a circuit diagram showing an equivalent circuit of components of the array sensor in the first embodiment.

FIG. 20 shows an example of a circuit diagram of a circuit equivalent to one APD pixel line 232 in the direction S1. One pair of a quenching resistor 226 and APD 227 respectively shown in FIG. 20 corresponds to one APD pixel 231. A terminal 2351 is equivalent to the pad 235, a terminal 2352 is connected to each APD pixel, and reverse voltage $V_R$ is applied. The APD 227 is operated in the Geiger mode by setting the reverse voltage $V_R$ so that it is equal to or higher than the breakdown voltage of the APD. Output electric signals (crest values of voltage and current or the quantity of charges) proportional to the sum of photons incident on the APD pixel line 232 in the direction S1 are acquired by adopting the configuration of the circuit shown in FIG. 20. Output electric signals (crest values of voltage and current or the quantity of charges) corresponding to each APD pixel line 232 in the direction S1 are converted from analog to digital and are output in parallel as digital signals in time series.

Since the individual APD pixel outputs only the similar pulse signal to that in a case where one photon is incident even if plural photons are incident in short time, total output signals in the PAD pixel line are not proportional to the number of incident photons when the number of photons incident on the individual APD pixel per unit time increases, and the linearity of signals is impaired. Besides, when incident light of fixed quantity (approximately mean one photon per one pixel) or more is incident on all pixels in the APD pixel line, output signals are saturated. The quantity of incident light per pixel can be reduced by adopting the configuration in which multiple APD pixels are arranged in the S1 direction and the more precise count of photons is enabled. For example, when the quantum efficiency of the APD pixel is 30%, sufficient linearity can be secured at optical intensity of approximately 1000 photons or less per unit time of detection by setting the number of pixels in the direction S1 to 1000, and optical intensity of approximately 3300 photons or less can be detected without being saturated.

To sense scattered light from the sample surface and detect from an infinitesimal defect to a relatively large defect at a signal level according to the dimensions, it is important to secure a dynamic range of the array sensor 224 that detects scattered light. To enlarge the dynamic range of the array sensor 224, the number of the APD pixels 231 shown in FIG. 19 and arranged in the S1 direction has only to be increased. However, when the total number of the APD pixel in the S1 direction is simply increased, there occurs a problem that stray capacitance increases by extending the dimension in the S1 direction and the operating speed is deteriorated, and also there occurs a problem that the mounting space increases in mounting the array sensor 224.

As a way to cope this, a method of reducing the dimensions of the APD pixel 231 and increasing the number of the APD pixels 231 arranged in the S1 direction without changing the whole length in the S1 direction is conceivable. However, when the whole dimensions of the APD pixel 231 are reduced, the numerical aperture of each APD pixel 231 is deteriorated, and the sensitivity of the array sensor 224 is deteriorated.

Then, in this embodiment, as shown in FIG. 19, the dynamic range is enlarged without increasing stray capacity by reducing the dimension in the direction S1 of the APD pixel 231 and increasing the number of the APD pixels 231 arranged in the S1 direction without changing the whole length in the S1 direction, the dimension in the S2 direction is increased, and the numerical aperture is prevented from being deteriorated without changing the area of the individual APD pixel 231. Hereby, required detection sensitivity is secured without deteriorating the operating speed even if the number of the APD pixels 231 arranged in the S1 direction is increased, and the dynamic range can be enhanced.

In the configuration of the plural-pixel sensor 224 shown in FIG. 18, since means for equalizing optical intensity distribution in the S1 direction is not particularly provided, the distribution of the quantity of light in the S1 direction of an optical image of a defect imaged on the conjugate plane 205 is projected on the plural-pixel sensor 224 as it is. Reflected and scattered light from the sample are effected by Gaussian distribution characteristic of the quantity of illumination light, their optical intensity is not even, and the optical intensity of an end is weak, compared with the center arranged in the S1 direction of the plural-pixel sensor 224. This means that the number of the effective APD pixels in the S1 direction decreases. The distribution in the S1 direction of the uniaxial enlarged image 225 of the defect can be made uniform by using, in place of the cylindrical lens, a lenticular lens where multiple minute cylindrical lenses having curvature in the S1 direction are arranged in the S1 direction, a diffractive optical element or an aspherical lens. Hereby, a range of optical intensity where linearity can be secured or an unsaturated range of optical intensity can be enlarged, keeping the number of the APD pixels in the S1 direction.

The number of photons at each position in the S2 direction on the conjugate plane 205 can be counted simultaneously and in parallel owing to the configuration of the abovementioned plural-pixel sensor 224.

Next, relation among the length of the light spot 20, the optical magnification of the detection unit 102 and the dimensions of the detection system 204 provided with the plural-pixel sensor will be described. When high-speed inspection is made at high sensitivity, the length of the light spot 20 is set to approximately 500 μm. When the detection system 204 provided with the plural-pixel sensor where 100 pixels are arrayed at the pitch of 25 μm in the S2 direction (100 APD pixel lines 232 are arrayed in S1 the direction) is installed, the optical magnification of the detection unit is 5 times and pitch between pixels projected on the sample surface is 5 μm.

When the sample is rotated at the rotating speed of 2000 rpm under the above-described condition, the whole surface of a circular sample having the diameter of 300 mm is scanned in 9 seconds and the whole surface of a circular sample having the diameter of 450 mm is scanned in 14 seconds. In the case of higher-speed inspection, the length of the light spot 20 is set to approximately 1000 μm. In this case, the optical magnification of the detection unit is 0.4 times and pitch between pixels projected on the sample surface is 62.5 μm. When the sample is rotated at the rotating speed of 2000 rpm on this condition, the whole surface of the circular sample having the diameter of 300 mm is scanned in 5 seconds and the whole surface of the circular sample having the diameter of 450 mm is scanned in 7 seconds.

Figure 21:
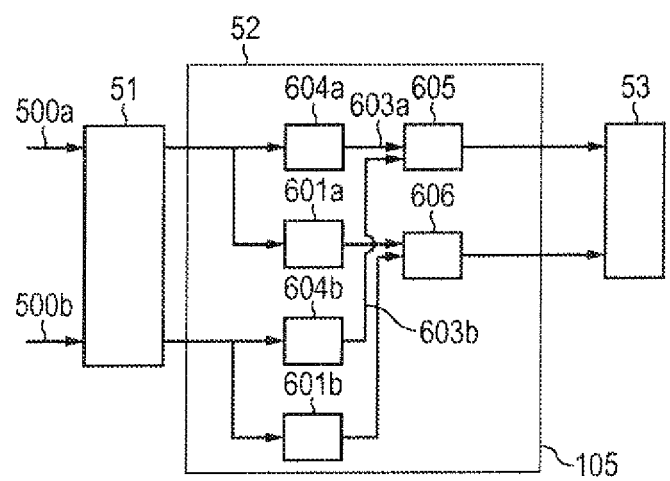
FIG. 21 is a block diagram showing one embodiment of a signal processing unit in the first embodiment of the present invention.

Next, the signal processing unit 105 that executes the classification of various types of defects and the estimate of the dimensions of the defects at high precision based upon scattered light intensity detection signals in various directions simultaneously detected by the plural detection optical systems that cover a wide angular range will be described in reference to FIG. 21. In this case, to simplify description, the configuration in a case where two detection systems 102a, 102b (not shown) in the detection unit 102 equipped with plural systems are provided of the signal processing unit 105 will be described below. Each detection system 102a, 102b outputs a signal for each APD pixel line. But in this case, description in view of a signal in one pixel line of the signals will be made below, although it goes without saying that the similar processing is also performed in parallel as to the other pixel lines.

Output signals 500a, 550b corresponding to the detected quantity of scattered light output from each detection elements provided to the detection systems 102a, 102b are input to a digital processor 52 via analog processors 51a, 51b in which each band-pass filter is built. In the digital processor 52, defect signals 603a, 603b are extracted by high-pass filters 604a, 604b and are input to a defect determination device 605. Since a defect is scanned in the S1 direction by the light spot 20, a waveform of the defect signal is acquired by magnifying or reducing an illuminance distribution profile in the S1 direction of the light spot 20. Accordingly, the SN ratio of the defect signals 603a, 603b is improved by passing the waveform of each defect signal through each high-pass filter 604a, 604b and cutting frequency bands including relatively much noise and a DC component. For each high-pass filter 604a, 604b, a high-pass filter having a specific cut-off frequency and designed so that components that are equal to or exceed the frequency are cut off or a band-pass filter or an FIR (Finite Impulse Response) filter similar to the waveform in which the shape of the light spot 20 is reflected of the defect signal is used.

The defect determination device 605 applies a threshold process to the input of the signal including the waveform of the defect output from each high-pass filter 604a, 604b and determines whether the defect exists or not. That is, since the defect signals based upon the detection signals from the plural detection optical systems are input to the defect determination device 605, the defect determination device 605 can perform high-sensitivity defect inspection by applying the threshold process to the sum of the plural defect signals and a weighted mean or ORing and ANDing a group of defects extracted by the threshold process applied to the plural defect signals on the same coordinates set on the surface of the wafer, compared with the detection of a defect based upon a single defect signal.

Further, the defect determination device 605 provides information on defect, which is determined to exist, including defect coordinates showing a position of the defect on the wafer calculated based upon the waveform of the defect and upon a sensitivity information signal and estimated values of the dimensions of the defect to the control unit 53 as defect information, and outputs them to the display unit 54 and others. The defect coordinates are calculated using the center of gravity of the waveform of the defect for a criterion. The dimensions of the defect are calculated based upon an integrated value or the maximum value of the waveform of the defect.

Furthermore, each output signal from the analog processor 51 is input to each low-pass filter 601a, 601b in addition to the high-pass filters 604a, 604b that configure the digital processor 52, and a low component of a frequency corresponding to the quantity of scattered light (haze) from minute roughness in the light spot 20 on the wafer and a DC component are output from each low-pass filter 601a, 601b. As described above, the output from each low-pass filter 601a, 601b is input to haze processing equipment 606 and there, the processing of haze information is executed. That is, the haze processing equipment 606 outputs a signal corresponding to a degree of haze every location on the wafer based upon the amplitude of an input signal acquired from each low-pass filter 601a, 601b as a haze signal. Besides, since the angular distribution of the quantity of scattered light from the roughness varies according to the spatial frequency distribution of the minute roughness, information of the spatial frequency distribution of the minute roughness can be acquired based upon the ratio in intensity of the haze signals and others from the haze processing equipment 606 by inputting the haze signal from each detector installed in mutually different azimuths and at different angles of the detection unit 102 to the haze processing equipment 606 as shown in FIGS. 13 to 23.

An example of a variation of illumination intensity distribution made on the sample surface by the illumination unit 101 will be described below. In place of the illumination intensity distribution (linearly) long in one direction and having substantially uniform intensity in the longitudinal direction, illumination intensity distribution having Gaussian distribution in the longitudinal direction can also be used. Gaussian distribution illumination long in one direction is formed by providing a spherical lens to the illumination intensity distribution controller 7, adopting a configuration in which an elliptic beam long in one direction is formed by the beam expander 5 or configuring the illumination intensity distribution controller 7 by plural lenses including a cylindrical lens.

Illumination intensity distribution long in one direction on the sample surface and narrow in width in a direction perpendicular to the direction is formed by installing a part or all of the spherical lenses or the cylindrical lenses respectively with which the illumination intensity distribution controller 7 is provided in parallel to the sample surface. The abovementioned illumination intensity distribution has characteristics that, compared with the case where uniform illumination intensity distribution is made, the variation of illumination intensity distribution on the sample surface due to the variation of a state of light incident on the illumination intensity distribution controller 7 is small and the stability of the illumination intensity distribution is high and, compared with a case where a diffraction optical element and a microlens array and others are used in the illumination intensity distribution controller 7, the transmittance of light is high and efficiency is satisfactory.

Figure 22A:
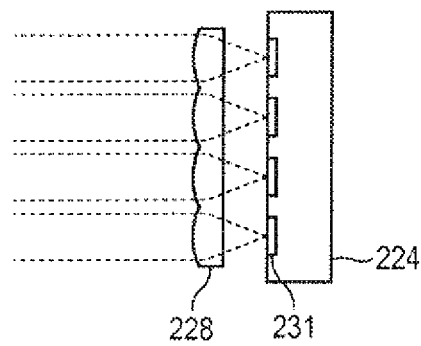
FIG. 22A is a side view showing the combination of the array sensor and a microlens array in the detection system provided with the plural-pixel sensor in the first embodiment of the present invention.
Figure 22B:
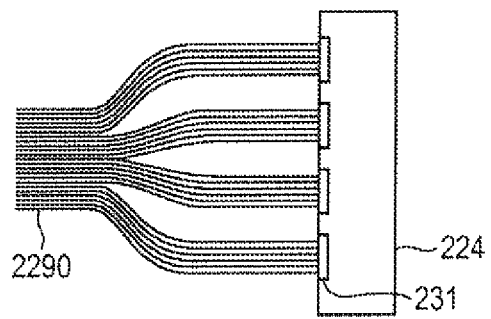
FIG. 22B is a side view showing the combination of an array sensor as a second example according to the present invention and an optical fiber array in the detection system provided with the plural-pixel sensor in the first embodiment of the present invention.

FIGS. 22A and 22B show the configuration of an example of a variation of the array sensor 224 shown in FIG. 18. As the area of a blind zone between APD pixels is relatively large, compared with the effective area of a light receiving surface of an APD pixel 231 when the individual APD pixel 231 is small in an array sensor 224 in which the APD pixels are arrayed, the array sensor has a problem that the numerical aperture of the array sensor 224 is deteriorated and light detection efficiency is deteriorated. Then, as shown in FIG. 22A, a rate of light incident on the blind zone between the APD pixels 231 is reduced by installing a microlens array 228 before the light receiving surface of the array sensor 224 and an effective numerical aperture can be enhanced. The microlens array 228 is acquired by arranging minute convex lenses at the same pitch as the array pitch of the APD pixels and is installed so that light (shown by a dotted line in FIG. 22A) parallel to a primary optical axis of incident light on the array sensor 224 is incident on the vicinity of the center of the corresponding APD pixel.

In the meantime, the configuration shown in FIG. 22B shows an example of a case where in place of the microlens array 228 shown in FIG. 22A, an optical fiber array 2290 is used.

Figure 23A:
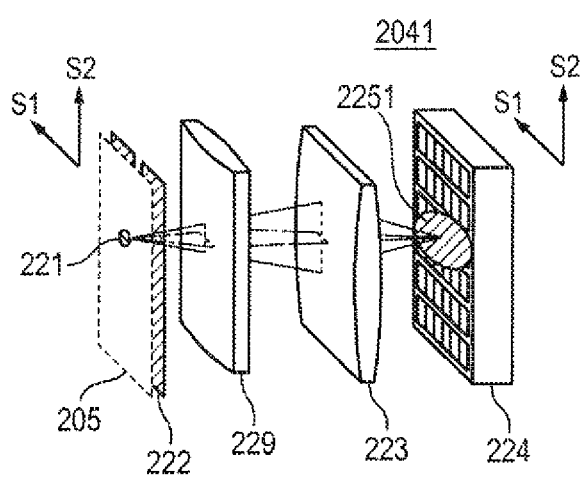
FIG. 23A is a perspective view showing the configuration of a variation 1 of the detection system provided with the plural-pixel sensor in the detection unit of the defect inspection device equivalent to the first embodiment of the present invention.

FIG. 23A shows the configuration of the first variation of the detection system 204 provided with the plural-pixel sensor. In this variation 1, a detection system 2041 provided with a plural-pixel sensor is provided with an uniaxial imaging system 229 having imaging function in the S1 direction and an uniaxial imaging system 223 having imaging function in the S2 direction. A defect image 221 is enlarged in the S1 direction by making imaging magnification in the S1 direction by the uniaxial imaging system 229 higher than imaging magnification in the S2 direction by the uniaxial imaging system 223.

When a cylindrical lens is used for the uniaxial imaging system 229 and the uniaxial imaging system 223, the magnification in the direction S1 is higher than the magnification in the direction S2 by installing the uniaxial imaging system 229 closer to a conjugate plane 205 than the uniaxial imaging system 223 and making imaging relation in the S1 direction. In the abovementioned configuration shown in FIG. 18, there is a case where the optical intensity distribution in the S1 direction of the uniaxial enlarged image 225 or the dimension of a spread of the image varies depending upon the angular distribution in the S1 direction of scattered light on the conjugate plane 205. In the meantime, in this variation, the size of an uniaxial enlarged image 2251 is determined by the size of a defect image 221 and imaging magnification in the S1 direction and in the S2 direction determined by the configurations and the arrangement of the uniaxial imaging system 229 and the uniaxial imaging system 223. Since the size of the defect image 221 of an infinitesimal defect is determined by the optical resolution of a detection unit 102 as described above, the size of the uniaxial enlarged image 2251 hardly varies and a stable detection result is acquired.

For an array sensor 224, a photomultiplier tube having a high electronic multiplication factor ($10^4$ or more) can also be used in place of the avalanche photodiode. The use of the avalanche photodiode has an advantage that the optical magnification of the detection unit 102 can be reduced because the size of an individual pixel can be reduced and the integration of several hundreds of or several thousands of pixels or more is enabled at a low cost, while the photomultiplier tube has an advantage that the dependency upon temperature of the multiplication factor of electrons is low and is stable.

Figure 23B:
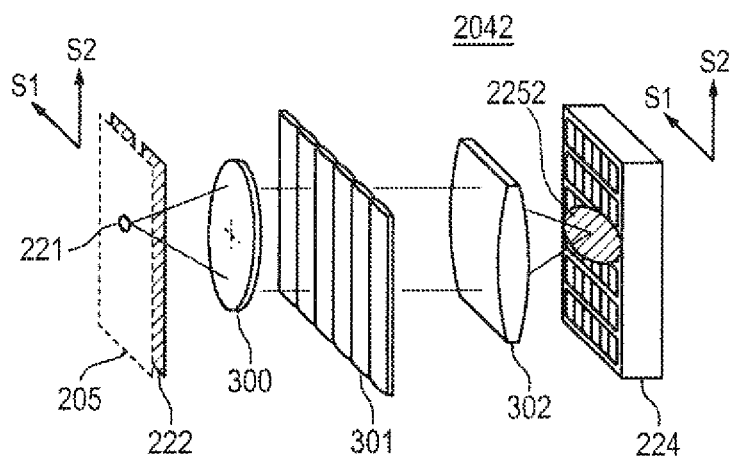
FIG. 23B is a perspective view showing the configuration of a variation 2 of the detection system provided with the plural-pixel sensor in the detection unit of the defect inspection device equivalent to the first embodiment of the present invention.

FIG. 23B shows the configuration of a detection system 2042 as the second variation of the detection system 204 provided with the plural-pixel sensor. The detection system 2042 is provided with a plural-pixel sensor in which a condenser lens 300, a cylindrical fly-eye lens 301 and an imaging lens 302 that images in an uniaxial direction of a direction S2 are used in place of the uniaxial imaging systems 229, 223 described in reference to FIG. 23A.

Figure 23C:
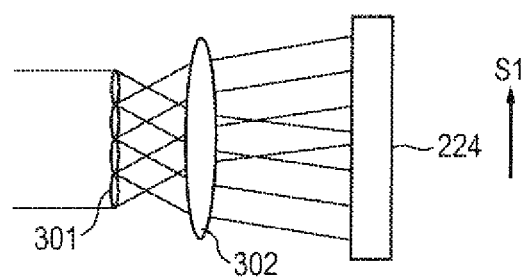
FIG. 23C is a plan view showing the configuration of the variation 2 of the detection system provided with the plural-pixel sensor in the detection unit of the defect inspection device equivalent to the first embodiment of the present invention.

In the variation 2, when light scattered from a defect image 221 on a conjugate plane 205 which is conjugate with a sample surface is converged by the condenser lens 300 and is made incident on the cylindrical fly-eye lens 301, plural minute luminous fluxes divided in a S1 direction are outgoing from the cylindrical fly-eye lens 301 as shown in FIG. 23C. The plural minute luminous fluxes outgoing from the cylindrical fly-eye lens 301 are incident on the imaging lens 302 that images in an uniaxial direction by being respectively diffused as light in which uniformity is enhanced in the S1 direction, are imaged in the S2 direction, and the plural minute luminous fluxes reach an array sensor 224 as light uniformly distributed in the S1 direction.

Scattered light from a defect on the sample in which the uniformity in the S1 direction is improved, compared with uniformity in the configuration in the variation 1 shown in FIG. 23A, can be detected by the array sensor 224 by adopting such configuration. As a result, a dynamic range of the array sensor 224 can be enlarged.

Figure 23D:
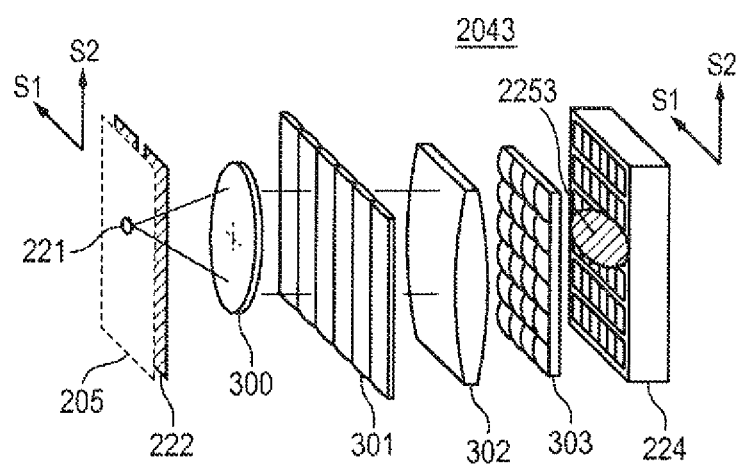
FIG. 23D is a perspective view showing the configuration of the variation 2 of the detection system provided with the plural-pixel sensor in the detection unit of the defect inspection device equivalent to the first embodiment of the present invention and shows a second example of the plural-pixel sensor in the detection unit according to the present invention.

Further, FIG. 23D shows the third variation of the detection system 204 provided with the plural-pixel sensor. In the configuration of a detection system 2043 provided with a plural-pixel sensor shown in FIG. 23D, the microlens array described in reference to FIG. 22A is inserted between the cylindrical fly-eye lens 301 and the array sensor 224 in the configuration of the detection system 2042 provided with the plural-pixel sensor in the variation 2 shown in FIG. 23B. The effective aperture ratio of the array sensor 224 can be improved by adopting such configuration, a dynamic range of the array sensor 224 is enlarged, and detection sensitivity can be further improved.

Figure 24A:
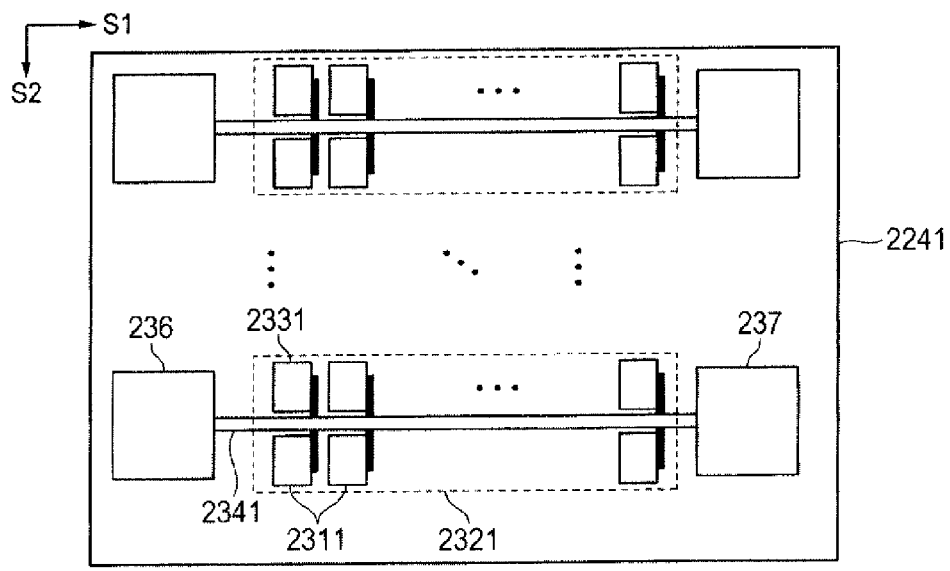
FIG. 24A is a front view showing a variation 1 of a sensor face of the array sensor in the detection system provided with the plural-pixel sensor in the detection unit in the first embodiment of the present invention.

FIG. 24A shows the first variation of the array sensor as a configuration for further improving the aperture ratio of the array sensor 224 described in reference to FIG. 19.

In an array sensor 2241 shown in FIG. 24A, two APD pixel lines encircled by a dotted line 2321 are set as one unit by connecting APD pixels 2311, 2331 having the similar shape to that of the array sensor 224 described in FIG. 19. The APD pixels 2331 in the upper line and the APD pixels 2311 in the lower line of the one unit 2321 of the array sensor 2241 are connected to a common wiring pattern 2341. In this case, an uniaxial imaging system 223 or 302 is configured as shown in FIG. 23A or FIGS. 23B and 23D so that an image of the scattered light from the defect projected on the array sensor 2241 is imaged on the two APD pixel lines.

An apparent aperture ratio can be improved by configuring the sensor array 2241 as described above, compared with the sensor array 224 shown in FIG. 19 though the resolution is deteriorated but detection sensitivity can be improved.

Further, as the APD pixels 2311, 2331 arranged in the upper and lower two lines share the wiring pattern 2341, the number of wiring can be reduced and the array sensory 2241 can be miniaturized.

Figure 25A:
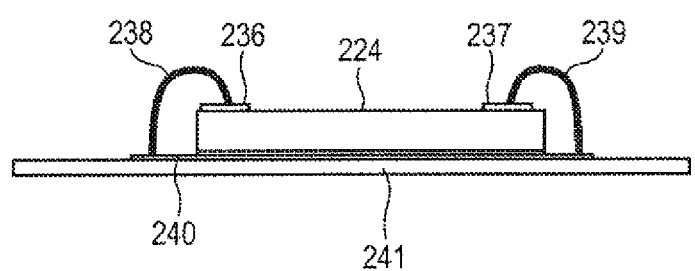
FIG. 25A is a side view showing a state in which pads of the array sensor in the detection system provided with the plural-pixel sensor in the detection unit in the first embodiment of the present invention and wiring on a substrate are connected via wire bonding.
Figure 25B:
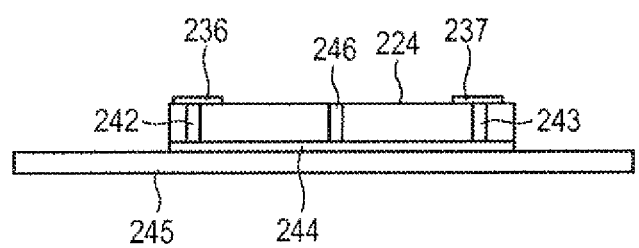
FIG. 25B is a sectional view showing a state in which pads of the array sensor in the detection system provided with the plural-pixel sensor in the detection unit in the first embodiment of the present invention and wiring on a substrate are connected via each through hole.

Further, stray capacity of the wiring is reduced by dividing the wiring pattern 2341 in two, providing electrode pads 236, 237 on both sides and reducing the substantial length of the wiring pattern and operating speed can be enhanced. In this case, signals from the electrode pads 236, 237 are transmitted to wiring 240 formed on a substrate 241 via wire bonding 238, 239 shown in FIG. 25A. Or as shown in FIG. 25B, signals from electrode pads 236, 237 are input to wiring 244 formed on the back of the array sensor 224 via through holes 242, 243 downward pierced from the electrode pads 236, 237. A reference numeral 246 denotes a through hole and the through hole is provided to connect the wiring 244 and an electrode (not shown) formed on a surface of the array sensor 224. Any or all of the through holes 242, 243, 246 are formed according to the configuration of the array sensor 224.

Figure 24B:
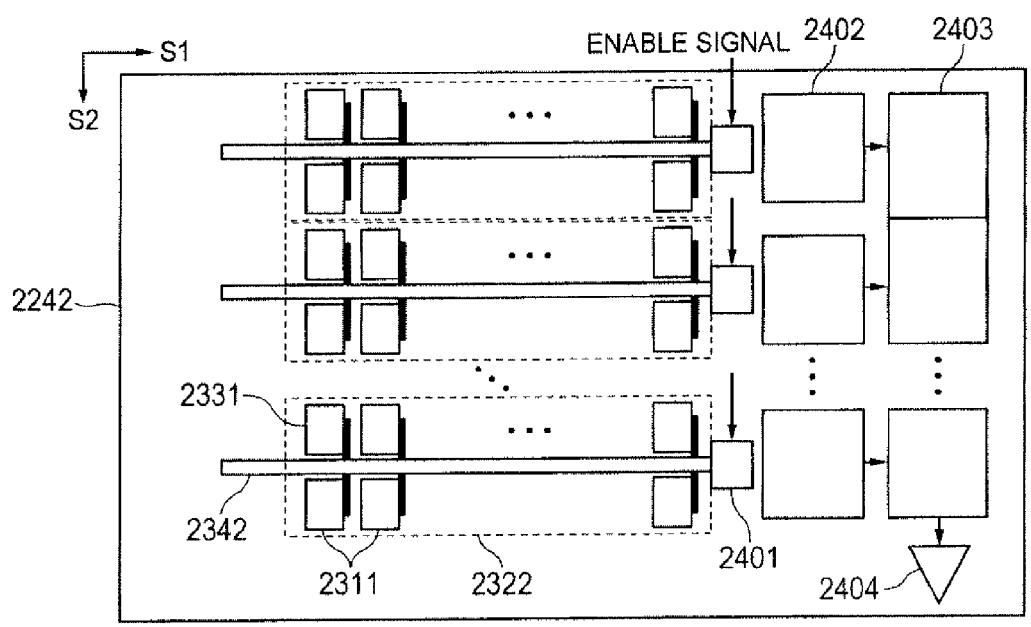
FIG. 24B is a front view showing a variation 2 of the sensor face of the array sensor in the detection system provided with the plural-pixel sensor in the detection unit in the first embodiment of the present invention.

FIG. 24B shows the second variation of the array sensor 224. In a sensor array 2242 shown in this example, APD pixels 2311, 2331 arranged in upper and lower two lines, similar to those shown in FIG. 24A, are set as one unit 2322 of the APD pixels by connecting the pixels to a common wiring pattern 2342. One end of the wiring pattern 2342 is connected to a transfer gate 2401. The transfer gate 2401 receives an enable signal synchronized with the oscillation of a pulse laser emitted from the laser source 2, synchronizes a detection signal output from the APD pixels in one unit 2322 with the oscillation of the pulse emitted from the pulse laser as the laser source 2, and inputs the detection signal to CCD 2402 for vertical transfer. The detection signal input to the CCD for vertical transfer 2402 is transferred to CCD for horizontal transfer 2403 at a predetermined line rate after the detection signal is stored by time for several pulses from the pulse laser. The detection signal transferred to the CCD for horizontal transfer 2403 is serially transferred to a charge voltage conversion element 2404, is converted to a voltage signal in the charge voltage conversion element 2404, and is serially output.

By configuring the sensor array 2242 as described above, a signal output from the charge voltage conversion element 2404 in the sensor array 2242 can be processed as in a case where an output signal from a one-dimensional image sensor (a CCD sensor) is handled as a picture signal.

Owing to the transfer gate 2401, noise caused by an after pulse and dark current can be reduced by configuring as outputting a detection signal from one unit 2322 of the APD pixels in synchronous with the oscillation of the pulse from the pulse laser by receiving an enable signal synchronized with the oscillation of a pulse laser emitted from the laser source 2, inputting the output detection signal to the CCD for vertical transfer 2402, and storing the signal for several pulses. Hereby, a minute detection signal when feeble scattered light from an infinitesimal defect is detected can be prevented from burying itself under noise and the detection sensitivity of the defect can be enhanced.

By configuring the sensor array 2242 as described above, circuit elements after the CCD for horizontal transfer 2403 are not required to be configured by circuit elements having an operating characteristic in a high-frequency band close to 100 MHz and processing can be executed in parallel in multiple stages by increasing the number of units 2322 of the APD pixels arranged in a S2 direction. Hereby, a relatively large region can be collectively inspected by extending the dimensions in the S2 direction of a light spot on which illumination light 20 is irradiated on a sample using the sensor array 2242 including multiple units 2322 of the APD pixels.

Figure 26:
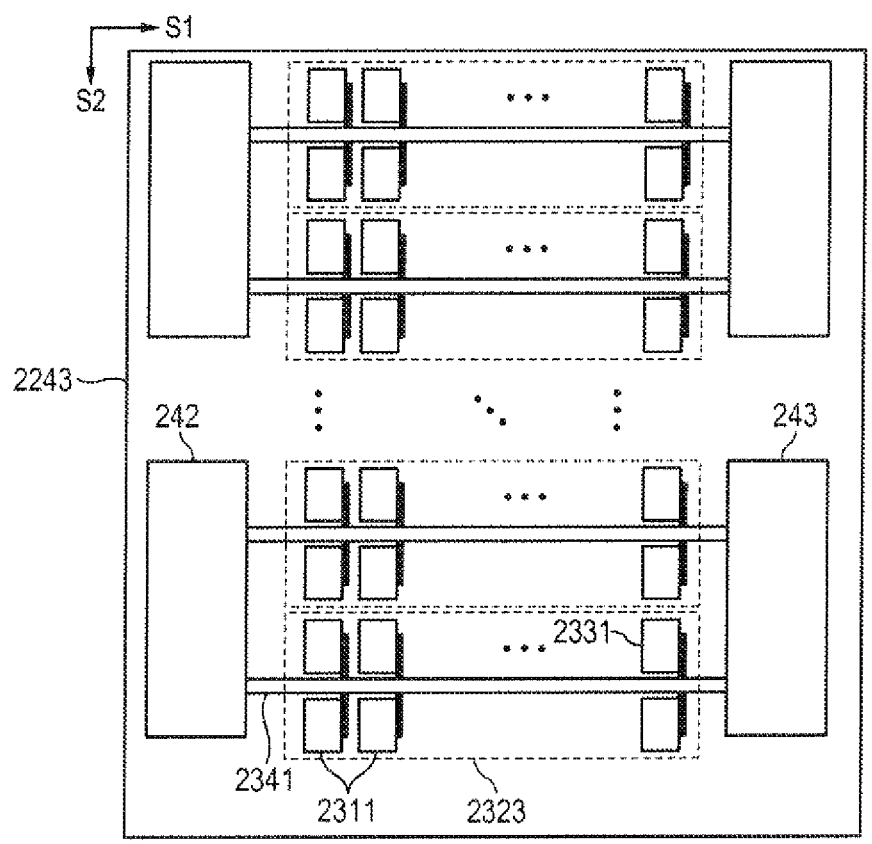
FIG. 26 is a front view showing a variation 3 showing the sensor face of the array sensor of the detection system provided with the plural-pixel sensor in the detection unit in the first embodiment of the present invention.

FIG. 26 shows an example of an array sensor 2243 in which the number of APD pixels included in a unit 2323 of APD pixels is further increased as the third variation of the array sensor 224 shown in FIG. 19.

In the array sensor 2243 shown in FIG. 26, electrode pads 242, 243 are configured by respectively coupling the electrode pads 236, 237 of the array sensor 2241 shown in FIG. 24A to upper or lower electrode pads. When the array sensor 2243 configured as described above is viewed as a one-dimensional image sensor in which plural pixels are arranged in a S2 direction, a dynamic range of a signal equivalent to one pixel output from the electrode pads 236, 237 can be further enlarged by increasing the number of APD pixels connected to the electrode pads 236, 237 respectively equivalent to one pixel of the one-dimensional image sensor though resolution as the one-dimensional image sensor is deteriorated.

Hereby, a defect of size in a relatively large range from a further infinitesimal defect in the order of a nanometer to a relatively large defect of approximately several μm can be detected.

Figure 27A:
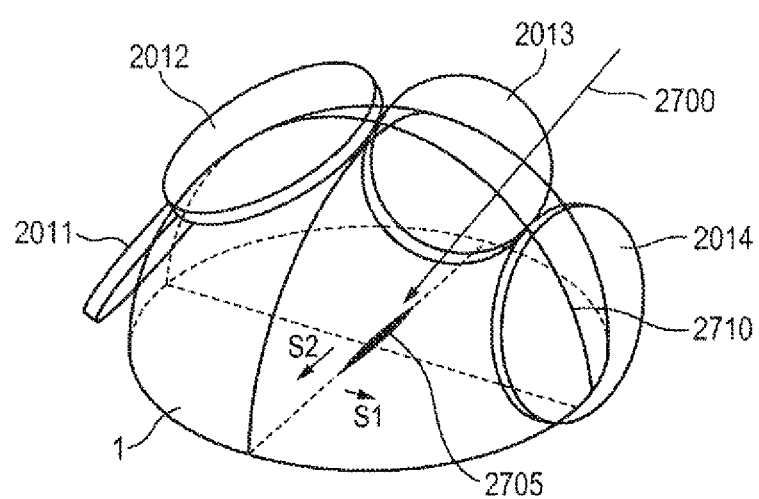
FIG. 27A is a perspective view showing a sample and objective lenses of plural detection systems in a state in which the plural detection systems are arranged on a meridian of a celestial sphere in the detection unit in the first embodiment of the present invention.

FIG. 27A schematically shows the arrangement of detection units 102 having a different configuration from the configurations shown in FIGS. 13 to 15. In FIG. 27A, the configuration in which a linear region 2705 on a sample 1 is illuminated from an oblique direction shown by an arrow 2700 based upon the sample 1 by the illumination unit 101 shown in FIG. 1, the plural detection units 102 are arranged in a direction perpendicular to a longitudinal direction of the linear region 2705 (in positions on a meridian 2710 of a celestial sphere from which the linear region 2705 on the sample 1 is visible) is shown. The plural detection units 102 are respectively configured using the configuration of the detection system 204 shown in any of FIGS. 18 to 26 in the optical system shown in FIG. 16. In FIG. 27A, lenses 2011 to 2014 are equivalent to the objective lens 201 of the detection unit 102 shown in FIG. 16. In the following description, to simplify description, a case where the configuration shown in FIG. 18 is used for the detection system 204 shown in FIG. 16 and the array sensor 224 having the configuration shown in FIG. 19 is used for the array sensor 224 shown in FIG. 18 will be described. However, the configurations shown in FIGS. 22A to 26 can also be similarly applied.

An optical image of scattered light from a defect in each detection unit 102 can be imaged on an APD pixel of an array sensor 224 by arranging the respective objective lenses 2011 to 2014 of the plural detection units 102 in a direction shown in FIG. 27A for the linear illuminated region 2705 on the sample 1 when the defect exists in the linearly illuminated region 2705 on the sample 1. Therefore, scattered light described in reference to FIG. 18 relatively long in a S1 direction and imaged in a S2 direction can be detected.

Figure 28A:
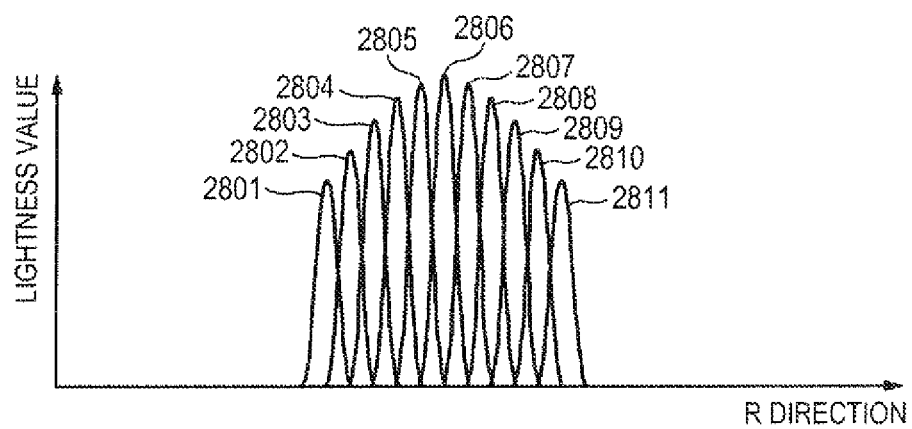
FIG. 28A is a graph showing output waveforms from array sensors of the detection systems arranged on the meridian of the celestial sphere in the detection unit in the first embodiment of the present invention.

When an optical image of scattered light from a defect is detected by the array sensor 224 of each detection unit 102 arranged as described above in a case where the defect exists in the linear illuminated region 2705 on the sample 1, a signal shown in FIG. 28A is respectively output from the array sensor 224 of each detection unit 102. In FIG. 28A, a waveform 2801 represents a waveform of a signal output from the pad 235 connected to the wiring pattern 234 connected to the APD pixel line 232 of the array sensor 224 shown in FIG. 19. A waveform 2811 represents a waveform of a signal output from a pad 235n shown in FIG. 19.

Since scattered light imaged in the direction S2 is detected on the array sensor 224, no scattered light is detected in a region on the left side of the waveform 2801 and in a region on the right side of the waveform 2811 in FIG. 28A.

Figure 27B:
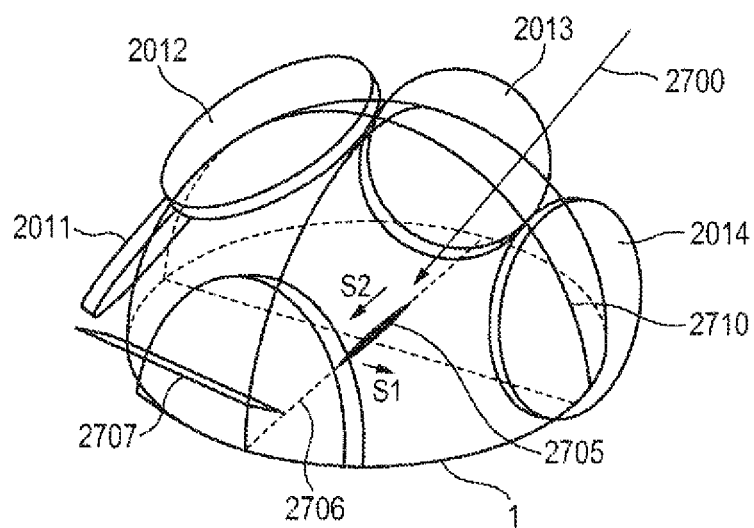
FIG. 27B is a perspective view showing the sample and objective lens of plural detection systems in a state in which the plural detection systems are arranged on a meridian of a celestial sphere and in a position in which forward scattered light is detected in the detection unit in the first embodiment of the present invention.

The configuration shown in FIG. 27B is acquired by adding a detection unit that converges and detects forward scattered light from an illuminated region 2705 with a lens 2706 when illumination light is irradiated onto the linear illuminated region 2705 on a sample 1 from a direction shown by an arrow 2700 to the configuration shown in FIG. 27A. When the sample 1 is made of silicon (Si), the information of a defect is generally often included in the forward scattered light. Lenses 2011 to 2014 are the same as those described in reference to FIG. 27A and are equivalent to the objective lens 201 of the detection unit 102.

Before the lens 2706 that converges the forward scattered light, a mirror 2707 for intercepting regularly reflected light from the linear illuminated region 2705 on the sample 1 by illumination light irradiated from the direction shown by the arrow 2700 is arranged so as to prevent regularly reflected light from the linear illuminated region 2705 on the sample 1 from being incident on the lens 2706. An angle of the mirror 2707 is set so that the regularly reflected light is not incident on any of the lenses 2011 to 2014. In place of the mirror 2707, an intercepting pattern may also be arranged.

Waveforms of signals detected via the lenses 2011 to 2014 and output from each array sensor 224 out of signals detected by each detection unit 102 arranged as shown in FIG. 27B are the same as the signal waveforms shown in FIG. 28A in the case shown in FIG. 27A. In the meantime, signal waveforms output from an array sensor 224 of the detection unit 102 that detects the forward scattered light passed through the lens 2706 cannot be imaged in a S2 direction on the array sensor 224 because the distances between each area in a longitudinal direction of the linear illuminated region 2705 on the sample 1 and the lens 2706 are different and the forward scattered light passed through the lens 2706 diverges in the S2 direction, and a broad signal is output from the array sensor 224.

Figure 28B:
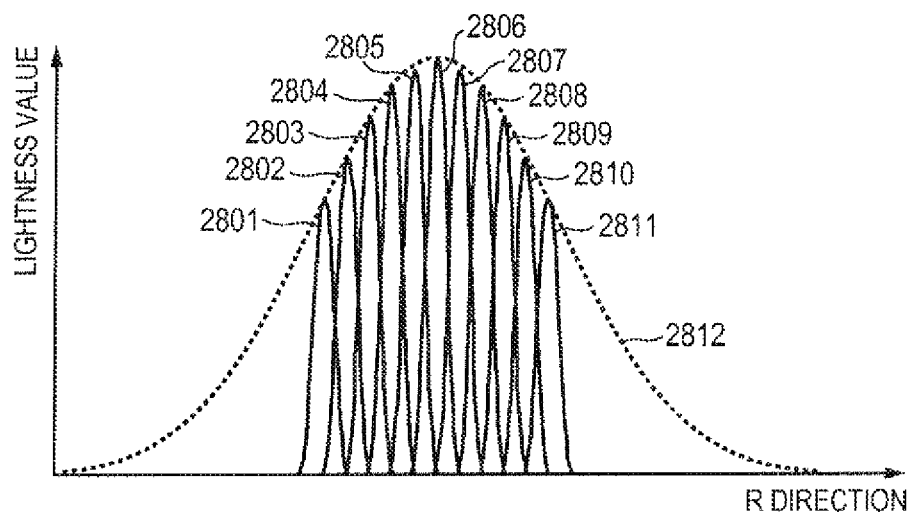
FIG. 28B is a graph showing a state in which output waveforms from array sensors of the detection systems arranged on the meridian of the celestial sphere and an output waveform from an array sensor that detects forward scattered light are overlapped in the detection unit in the first embodiment of the present invention.

FIG. 28B shows an example of a signal acquired by superimposing a signal detected by the array sensor 224 through the lens 2012 and a signal detected by the array sensor 224 through the lens 2706 for example in the configuration shown in FIG. 27B. Signals 2801 to 2811 detected through the lens 2012 have the same signal waveforms as those shown in FIG. 28A, while the signal detected through the lens 2706 has divergence in the S2 direction because the signal is not imaged in the S2 direction to be a broad signal shown by a broken light 2812.

Figure 12:
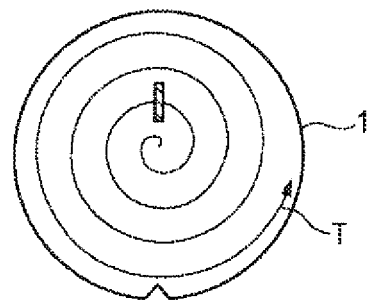
FIG. 12 is a plan view according to the present invention showing a locus of a light spot by the scanning of the surface of the sample by the illumination unit of the defect inspection device equivalent to the first embodiment of the present invention.
Figure 29A:
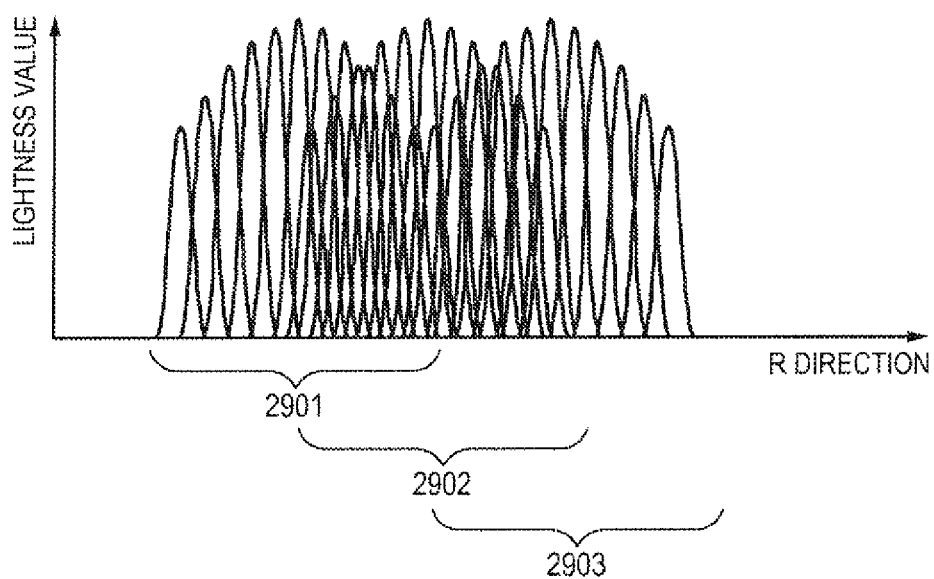
FIG. 29A is a graph showing output waveforms from the array sensors when a position of the same angle of rotation on a sample is detected by the detection systems arranged on the meridian of the celestial sphere in the detection unit in the first embodiment of the present invention in a case where the sample is spirally scanned by illumination light.

FIG. 29A shows an example of output signal waveforms in the same rotation angle position when the sample is rotated three times when illumination light is radially shifted and is spirally irradiated on the sample 1, rotating the sample as shown in FIG. 12. Scattered light from a position displaced radially (in a direction shown by an arrow R) by the quantity of radial feed pitch is detected every rotation. In this example, the radial feed pitch every rotation of the sample 1 is made shorter than the length in the S2 direction of the illuminated region 2705 (20 in FIG. 11) so that the same location on the sample 1 is detected plural times. Further, the radial feed pitch every rotation is set to displaced quantity by integral times of pitch between the APD pixel lines including the APD pixels 231 in the S2 direction when the surface of the sample 1 is projected on the array sensor 224.

As shown in FIG. 19 for example, an image of scattered light from a defect is imaged between the APD pixel line 232 of the array sensor 224 and the APD pixel line adjacent in the S2 direction at the time of first rotation by setting the feed pitch of the illuminated region 2705 every rotation of the sample 1 to the displaced quantity by integral times of pitch in the S2 direction between the APD pixels 231 as described above, and even if no defect is detected in any pixel line, the image of scattered light from the defect is imaged on some APD pixel line because the feed pitch of the illuminated region 2705 is not the integral times of the APD pixel line in the S2 direction on the array sensor 224 when the sample 1 is rotated once. A contrary case is possible, however, in any case, possibility that a defect is overlooked can be reduced.

Besides, the detection of plural times of the same location on the sample 1 by spirally illuminating the sample 1 with illumination light means that the same location on the sample 1 is detected in different APD pixel lines on the array sensor 224 and the effect that dispersion in detection sensitivity between the APD pixel lines can be equalized is also obtained.

Generally, a peak position (a central position of a defect) can be acquired from an equalized waveform based upon the knowledge that scattered light from the defect on a sample has Gaussian distribution, and the peak position can be detected at higher precision compared with a case of the feed pitch of integral times of a pixel.

Figure 29B:
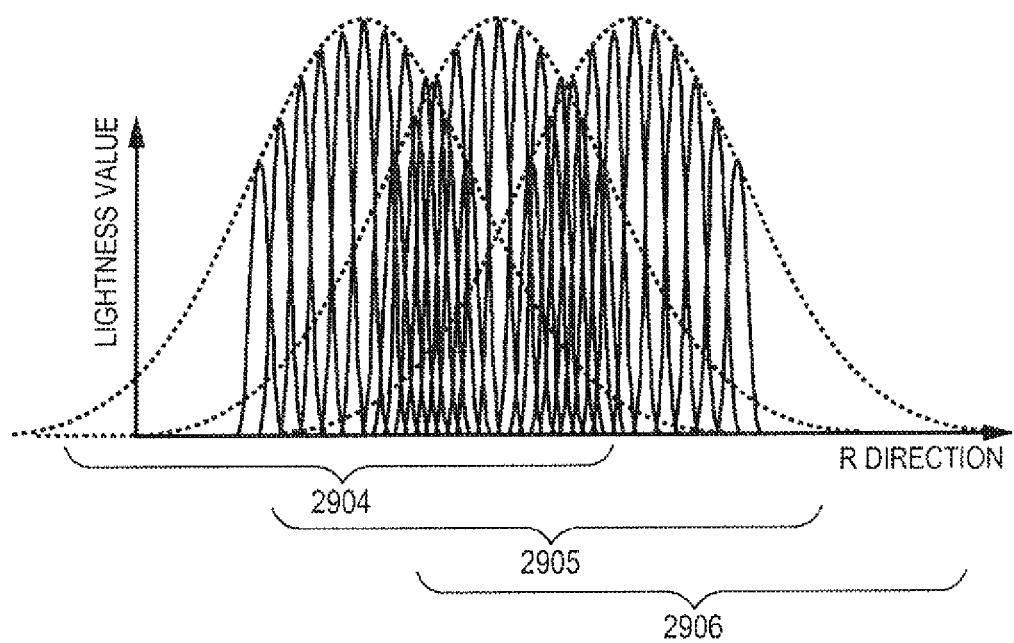
FIG. 29B is a graph showing that output waveforms from the array sensors when the position of the same angle of rotation on the sample is detected by the detection systems arranged on the meridian of the celestial sphere and an output waveform from the array sensor that detects forward scattered light are overlapped in the detection unit in the first embodiment of the present invention in the case where the sample is spirally scanned by illumination light.

FIG. 29B shows two signal waveforms in a state in which a signal detected on the array sensor 224 through the lens 2012 for example and a signal detected on the array sensor 224 through the lens 2706 in the configuration shown in FIG. 27B when the sample 1 is spirally illuminated in a rotated state are overlapped.

In this case, a peak position (a central position of a defect) can also be detected at higher precision based upon an equalized waveform by setting to the similar feed pitch to that shown in FIG. 29A as described in reference to FIG. 29A.

Moreover, in the case of a defect having a scattering characteristic that forward scattered light is intense and upward and sideway scattered light is feeble, the possibility that the defect is overlooked can be reduced by using a signal acquired by detecting the forward scattered light on the array sensor 224 through the lens 2706, compared with a case where no detection signal based upon forward scattered light is used as shown in FIG. 29A. That is, the detection of more various defects is made possible by providing the optical system which detects forward scattered light as shown in FIG. 27B.

Second Embodiment

Next, an example in which the detection unit 102 described in the first embodiment is applied to an inspection device using a illumination unit different from the illumination unit 101 shown in FIG. 1 will be described in reference to FIG. 30.

Figure 30:
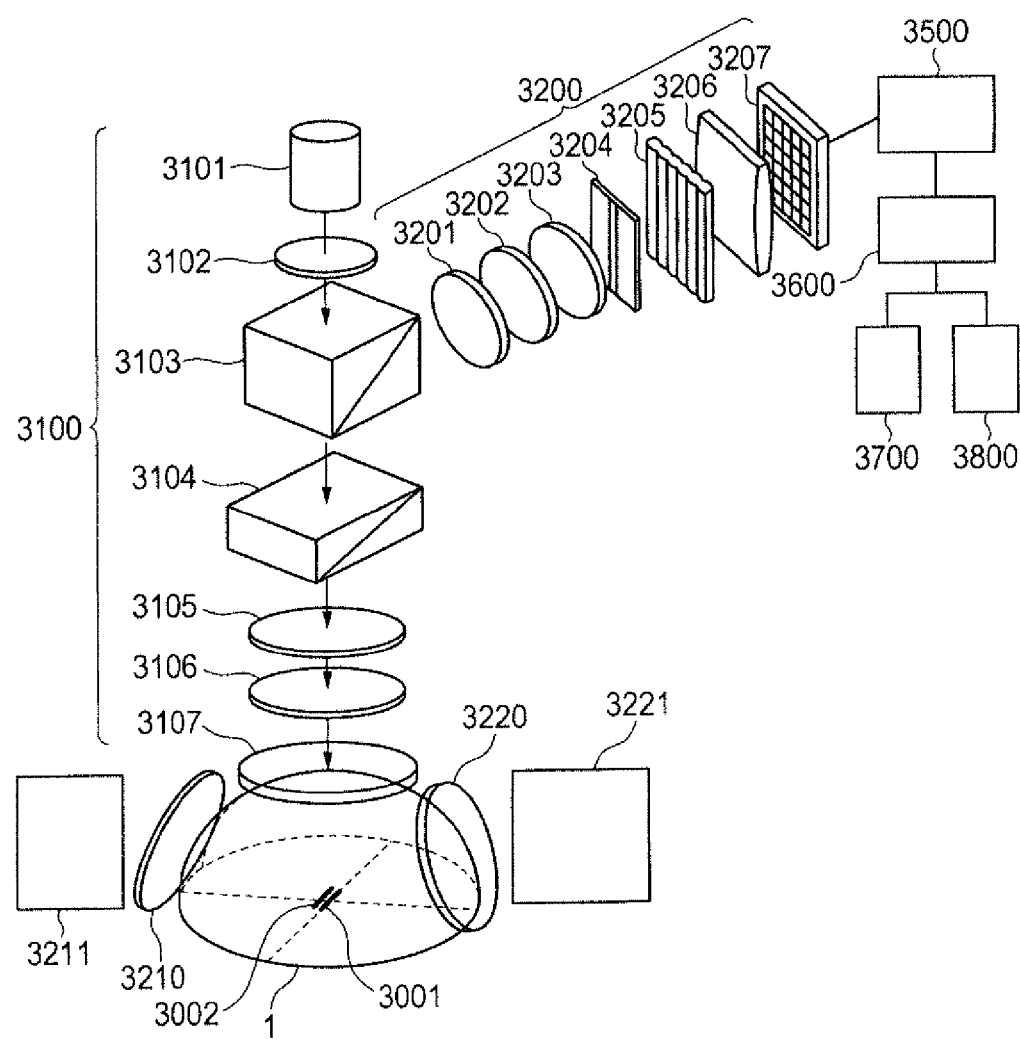
FIG. 30 is a block diagram showing the whole schematic configuration of a defect inspection device equivalent to a second embodiment of the present invention.

FIG. 30 shows the inspection device provided with the illumination unit 3100, the detection unit 3200 and lenses 3210, 3220. However, the inspection device is also provided with an optical system having the similar configuration to that of the detection unit 3200 at the subsequence stage of each lens 3210, 3220. And the inspection device is provided with a signal processing unit 3500, a control unit 3600, an input unit 3700 and a display unit 3800 which are respectively similar to each unit shown in FIG. 1. In the inspection device shown in FIG. 30, an example in which the configuration in the second variation of the detection system 204 shown in FIG. 23B provided with the plural-pixel sensor is adopted for the detection unit 3200 will be described below. However, in this embodiment, the configurations of the detection unit 3200 and a detection system 204 provided with a plural-pixel sensor provided at the subsequent stage of each lens 3210, 3220 are not limited to the configuration described in reference to FIG. 23B and the configurations described in reference to FIGS. 18, 23A, 23D may also be adopted.

In the configuration shown in FIG. 30, the reference numeral 3101 denotes an illumination light source and the illumination source oscillates an ultraviolet or vacuum ultraviolet laser beam having a short wavelength (wavelength: 355 nm or shorter) as in the first embodiment. The reference numeral 3102 denotes a polarizing plate and the polarizing plate applies a desired polarization property to a laser beam oscillated from the illumination light source 3101. The reference numeral 3103 denotes a polarized beam splitter (PBS) and the polarized beam splitter selectively transmits the laser beam to which the desired polarization property is applied by the polarizing plate 3102. The reference numeral 3104 denotes a birefringence prism. The birefringence prism branches the laser beam transmitted in the PBS 3103 into two luminous fluxes, and emits two beams. As for the laser beam branched into the two fluxes in the birefringence prism 3104, an oscillation direction of polarized light is turned in the half-wave plate 3105, the polarized light is turned circularly polarized light in the quarter-wave plate 3106, and transmitted through the objective lens 3107, and the circularly polarized light simultaneously illuminates slightly distant regions 3001, 3002 on the surface of the sample 1.

Light incident on the objective lens 3107 of light reflected and scattered upward from the slightly distant regions 3001, 3002 on the surface of the sample 1 on which the laser beam branched into the two fluxes are irradiated is transmitted in the quarter-wave plate 3106 to be linearly polarized light, and after the linearly polarized light is transmitted through the half-wave plate 3105, it incidents on the birefringence prism (Nomarski prism) 3106 and is synthesized to be one luminous flux. The synthesized one luminous flux is incident on the PBS 3103 and light having a specific polarized component (for example, a p-polarized component) of the reflected and scattered light from the sample 1 is reflected in a direction of the detection unit 3200 by the PBS 3103.

The light reflected in the direction of the detection unit 3200 is incident on an imaging lens 3201 and passes through a shielding slit 3203 arranged on a conjugate plane 3202 (equivalent to the conjugate plane 205 which is conjugate with the surface of the sample in FIG. 23B) which is conjugate with the surface of the sample 1 for the objective lens 3107 and the imaging lens 3201. The light that passes through the shielding slit 3203 is imaged on an array sensor 3207 in the S2 direction by a condenser lens 3204, a cylindrical fly-eye lens 3205 and an uniaxial imaging system 3206 that converges in an uniaxial direction which are respectively configured like the optical system shown in FIG. 23B, and the light is projected as light having width in the S1 direction. The array sensor 3207 is the same as the array sensor 224 described in reference to FIG. 23B.

When there is a slight difference in a level between the region 3001 and the region 3002 on which the illumination light is respectively irradiated on the surface of the sample 1, a difference in optical path length occurs between light which is incident on and reflected from the region 3001 and light which is incident on and reflected from the region 3002. When the lights having the difference in optical path length as described above are synthesized by the birefringence prism 3106, interference occurs. An image of reflected interferential light from the sample 1 is formed on the conjugate plane 3202, and the image is projected on the array sensor 3207 by forming an image in the S2 direction and a light having width in the S1 direction.

The minute difference in a level on the sample 1 can be detected by processing a signal telling the detection of the differential interference contrast image of the sample surface 1 projected on the array sensor 3207.

In the meantime, scattered light in a direction of the objective lens 3210 from the region 3001 and the region 3002 respectively illuminated through the objective lens 3107 is converged by the objective lens 3210 and is detected by a detection optical system 3211 arranged at the subsequent stage of the objective lens 3210 and having the same configuration as the detection unit 102 shown in FIG. 16. Since the configuration of the detection optical system 3211 is the same as those shown in FIGS. 16 and 23B, the description is omitted.

Similarly, the light scattered in a direction of the objective lens 3220 from the region 3001 and the region 3002 respectively illuminated through the objective lens 3107 is converged by the objective lens 3220, and is detected by a detection optical system 3221 installed at the subsequent stage of the objective lens 3220 and having the same configuration as the detection unit 102 shown in FIG. 16. Since the configuration of the detection optical system 3221 is the same as those shown in FIGS. 16 and 23B, the description is omitted.

A signal processing unit 3500 receives and processes the signal output from the array sensor 3207 in the detection unit 3200, and detects the minute difference in a level on the sample 1. Besides, a detection signal of the scattered light detected by the detection optical system 3211 through the objective lens 3210 and a detection signal of the scattered light detected by the detection optical system 3221 through the objective lens 3220 are both input to the signal processing unit 3500, and processed there, and the defect on the sample 1 is detected.

On a display unit 3800, the minute difference in a level of the sample 1 detected by the signal processing unit 3500 and the information of the defect are displayed together with positional information on the wafer.

The present invention is not limited to the abovementioned embodiments and includes various variations. For example, the abovementioned embodiments are detailed description for clarifying the present invention and the present invention is not necessarily limited to all the described configurations. Besides, in place of a part of the configuration in the certain embodiment, the configuration in the other embodiment can also be used and moreover, the configuration in the other embodiment can also be added to the configuration in the certain embodiment. Further, another configuration can be added, deleted or used to/from/ in place of a part of the configuration of each embodiment.

LIST OF REFERENCE SIGNS

2: Laser source, 5: Beam expander, 6: Polarization controller, 7: Illumination intensity distribution controller, 24: Illumination intensity distribution monitor, 53: Control unit, 54: Display unit, 55: Input unit, 101: Illumination unit, 102: Detection unit, 103: Stage unit, 105: Signal processing unit, 201: Objective lens, 202: Polarization filter, 203: Imaging lens, 204: Detection system provided with plural-pixel sensor, 224, 2241, 2242, 2243: Array sensor.

The invention claimed is:

1. A defect inspection method comprising:
    detecting light which is reflected and scattered from a linear region on a surface of the sample on which the light is irradiated; and
    detecting a defect on the sample, wherein the step of detecting the defect includes:
        enlarging the reflected and scattered light from the sample in one direction and imaging the light in a direction perpendicular to the one direction;
        detecting the reflected and scattered light enlarged in the one direction and imaged in the direction perpendicular to the one direction by an array sensor comprising detection pixels that are arranged in a two-dimensional grid;
        generating an output signal from each detection pixel of the array sensor, wherein the detection pixels of the array sensor are arranged in the two-dimensional grid in a direction in which the reflected and scattered light is enlarged; and
        sequentially extracting a signal, which is acquired by adding the output signals from each detection pixel arranged in the direction in which the reflected and scattered light is enlarged, in one direction in which the light is imaged.

2. The defect inspection method according to claim 1, wherein the reflected and scattered light diffused in the one direction and imaged in the direction perpendicular to the one direction is detected by the array sensor where the detection pixels having a longer dimension in a direction perpendicular to the one direction in which the reflected and scattered light is imaged are arranged two-dimensionally.

3. The defect inspection method according to claim 1, wherein the enlargement in the one direction and the imaging in the direction perpendicular to the one direction is conducted as, when the linear region on the surface of the sample on which the light is irradiated is projected on the array sensor, a width of the light which is a direction perpendicular to a longitudinal direction of the linear region is the one direction of the enlargement and the longitudinal direction of the linear region is the direction of the imaging perpendicular to the one direction.

4. The defect inspection method according to claim 1, wherein the enlargement is performed by magnifying the reflected and scattered light in the one direction.

5. The defect inspection method according to claim 1, wherein the enlargement is performed by enlarging the reflected and scattered light in the one direction with a cylindrical fly-eye lens.

6. The defect inspection method according to claim 1, wherein a defect on the sample is detected by detecting reflected and scattered light from the linear region on the sample, on which light is irradiated, in a plurality of directions and processing a signal acquired by detecting in the plurality of directions.

7. The defect inspection method according to claim 1, wherein detection is performed by detecting light reflected and scattered from the linear region, on which the light is irradiated, to a longitudinal direction of the linear region by enlarging in one direction and imaging in the direction perpendicular to the one direction.

8. The defect inspection method according to claim 1, wherein the detection of reflected and scattered light from the sample includes:
    detecting light reflected and scattered from the linear region, on which the light is irradiated, to a direction perpendicular to a longitudinal direction of the linear region by enlarging in one direction and imaging in the direction perpendicular to the one direction by the array sensor in which the detection pixels are arranged two-dimensionally; and
    detecting light which is scattered from the linear region, on which the light is irradiated, to the longitudinal direction of the linear region by an array sensor in which the detection pixels are arranged two-dimensionally.

9. A defect inspection device comprising:
    detection unit configured to detect light which is reflected and scattered from a linear region on the sample on which the light is irradiated; and
    signal processing unit configured to process a signal acquired by detecting the reflected and scattered light and detect a defect on the sample,
    a detection unit configured to detect a defect on the sample, wherein the detection unit is provided with:
        an optical system configured to diffuse, in one direction, light which is reflected and scattered from the sample and image the light in a direction perpendicular to the one direction; and
        a detection system that is provided with an array sensor comprising detection pixels that are arranged in a two-dimensional grid, wherein the detection system is configured to detect the reflected and scattered light enlarged in the one direction by the optical system and imaged in the direction perpendicular to the one direction by the array sensor, and generate an output signal of each detection pixel of the array sensor, wherein the detection pixels of the array sensor are arranged in the two-dimensional grid in the direction in which the reflected and scattered light is enlarged.

10. The defect inspection device according to claim 9, wherein the two-dimensionally arranged detection pixels of the array sensor of the detection system have a long dimension in a direction which is perpendicular to the one direction where the reflected and scattered light is enlarged and in which the reflected and scattered light is imaged.

11. The defect inspection device according to claim 9, wherein when an image of the linear region, on which light is irradiated on the surface of the sample, is projected on the array sensor in the detection system that enlarges light which is reflected and scattered from the sample in the one direction and images the light in the direction perpendicular to the one direction, a width of the light which is a direction perpendicular to a longitudinal direction of the linear region is the one direction of enlargement and the longitudinal direction of the linear region is the direction of imaging perpendicular to the one direction.

12. The defect inspection device according to claim 9, wherein the optical system is provided with lenses, and wherein the enlargement in the one direction of the reflected and scattered light from the sample is performed by magnifying the reflected and scattered light in the one direction by the lenses.

13. The defect inspection device according to claim 9,
wherein the optical system is provided with a cylindrical fly-eye lens, and
wherein the enlargement in the one direction of the reflected and scattered light from the sample is performed by enlarging the reflected and scattered light in the one direction with the cylindrical fly-eye lens.

14. The defect inspection device according to claim 9,
wherein the detection unit installs a plurality of detection subunits,
wherein the plurality of detection subunits detect lights which are reflected and scattered from the linear region on the sample, on which light is irradiated, to a plurality of directions; and
wherein the signal processing unit detects a defect on the sample by processing respective signals acquired by detecting the reflected and scattered light by the plurality of directions of the plurality of detection subunits.

15. The defect inspection device according to claim 9,
wherein the detection unit is arranged in a direction perpendicular to a longitudinal direction of the linear region on which light is irradiated on the sample;
the optical system enlarges, in one direction, light which is reflected and scattered from the linear region on the sample on which the light is irradiated and images the light in a direction perpendicular to the one direction; and
the detection system detects light enlarged in the one direction imaged in the direction perpendicular to the one direction.

16. The defect inspection device according to claim 9, wherein the detection unit is provided with:
the optical system that is arranged in a direction perpendicular to a longitudinal direction of the linear region on which light is irradiated on the sample, enlarges, in one direction, light that is reflected and scattered from the linear region where the light is irradiated on the sample and images the light in a direction perpendicular to the one direction;
the detection system that detects light enlarged in the one direction and imaged in the direction perpendicular to the one direction;
further, a convergent optical system that converges light which is scattered in a longitudinal direction of the linear region from the linear region on which the light is irradiated on the sample; and
a convergent detection system that detects light converged by the convergent optical system.

* * * * *